United States Patent
Kondo et al.

(10) Patent No.: US 10,029,021 B2
(45) Date of Patent: Jul. 24, 2018

(54) POLYMER, CONTRAST AGENT FOR NUCLEAR MAGNETIC RESONANCE ANALYSIS OR MAGNETIC RESONANCE IMAGING USING THE POLYMER, COMPOUND AND METHOD OF NUCLEAR MAGNETIC RESONANCE ANALYSIS AND METHOD OF MAGNETIC RESONANCE IMAGING USING THE POLYMER

(71) Applicant: CANON KABUSHIKI KAISHA, Tokyo (JP)

(72) Inventors: Teruyuki Kondo, Kyoto (JP); Yasuhiro Aoyama, Kyotanabe (JP); Hisatsugu Yamada, Kyoto (JP); Yoshinori Hasegawa, Kyoto (JP); Hidehito Tochio, Kyoto (JP); Yu Kimura, Kyoto (JP); Masahiro Shirakawa, Kyoto (JP); Fuminori Sugihara, Ibaraki (JP); Tetsuya Matsuda, Kyoto (JP); Shinsuke Sando, Fukuoka (JP); Masato Minami, Kawasaki (JP); Fumio Yamauchi, Kyoto (JP); Tetsuya Yano, Kyoto (JP); Hidetoshi Tsuzuki, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 482 days.

(21) Appl. No.: 14/395,193

(22) PCT Filed: May 22, 2013

(86) PCT No.: PCT/JP2013/064819
§ 371 (c)(1),
(2) Date: Oct. 17, 2014

(87) PCT Pub. No.: WO2013/176292
PCT Pub. Date: Nov. 28, 2013

(65) Prior Publication Data
US 2015/0071861 A1 Mar. 12, 2015

(30) Foreign Application Priority Data

May 23, 2012 (JP) ................................ 2012-118061

(51) Int. Cl.
*A61K 49/12* (2006.01)
*C08F 30/02* (2006.01)

(52) U.S. Cl.
CPC ............ *A61K 49/126* (2013.01); *A61K 49/12* (2013.01); *C08F 30/02* (2013.01)

(58) Field of Classification Search
CPC ........ A61K 49/12; A61K 49/126; C08F 30/02
See application file for complete search history.

(56) References Cited

U.S. PATENT DOCUMENTS

| | | | |
|---|---|---|---|
| 6,210,655 B1 | 4/2001 | Stein | |
| 6,492,147 B2 | 12/2002 | Imamura et al. | |
| 7,465,779 B2 | 12/2008 | Kenmoku et al. | |
| 7,470,768 B2 | 12/2008 | Kenmoku et al. | |
| 7,527,809 B2 | 5/2009 | Yano et al. | |
| 7,557,176 B2 | 7/2009 | Kenmoku et al. | |
| 8,481,254 B2 | 7/2013 | Yamauchi et al. | |
| 8,765,432 B2 * | 7/2014 | Charles | A61K 47/48176 435/188 |
| 8,815,485 B2 | 8/2014 | Tanaka et al. | |
| 2010/0247444 A1 | 9/2010 | Yoshimura et al. | |
| 2011/0065212 A1 | 3/2011 | Ban et al. | |
| 2011/0117023 A1 * | 5/2011 | Yamauchi | A61K 41/00 424/9.1 |
| 2013/0288345 A1 | 10/2013 | Yamauchi et al. | |
| 2014/0235775 A1 | 8/2014 | Tanaka et al. | |
| 2015/0004538 A1 | 1/2015 | Kawamura et al. | |

FOREIGN PATENT DOCUMENTS

| | | | |
|---|---|---|---|
| EP | 2 020 244 A1 | 2/2009 | |
| JP | 2009-079046 A | 4/2009 | |
| WO | 91/12824 A2 | 9/1991 | |
| WO | 2008/059835 A1 | 5/2008 | |
| WO | 2009/031712 A1 | 3/2009 | |
| WO | 2009/046457 A2 | 4/2009 | |
| WO | WO2011/130694 | * 10/2011 | .............. C07L 77/02 |

OTHER PUBLICATIONS

J.-J. Yuan et al., "Synthesis of Biocompatible Poly[2-(methacryloyloxy)ethyl phosphorylcholine]-Coated Magnetite Nanoparticles," 22(26) Langmuir 10989-10993 (Nov. 2006) (XP055096395).
Jan-Bernd HOvener et al., "PASADENA hyperpolarization of 13C Biomolecules: Equipment Design and Installation," 22(2) Magn. Reson. Mater. Phys. pp. 111-121 (Apr. 2009) (XP002538149).
Communication pursuant to Article 94(3) EPC in European Application No. 13729817.0 (dated Oct. 2, 2017).

* cited by examiner

*Primary Examiner* — Michael G Hartley
*Assistant Examiner* — Leah H Schlientz
(74) *Attorney, Agent, or Firm* — Fitzpatrick, Cella, Harper & Scinto

(57) ABSTRACT

As a substance used as a contrast agent for a method of nuclear magnetic resonance analysis or a method of magnetic resonance imaging, a substance with high selectivity and high sensitivity was demanded. According to the present invention, when a polymer having, in a side chain thereof, a sequence of a $^1H-^{13}C-^{15}N$, $^1H-^{15}N-^{13}C$ or $^1H-^{13}C-^{13}C$ bond, that is, a structure labeled with stable isotopes of $^{13}C$ and $^{15}N$, is used, the abundance of such a sequence in one molecule can be increased, and hence, high selectivity and higher sensitivity can be attained when used as a contrast agent.

23 Claims, 9 Drawing Sheets

$M_n=5000, M_p=5000, M_w=5500, PDI=1.17$ $M_n=12000, M_p=14000, M_w=14000, PDI=1.14$

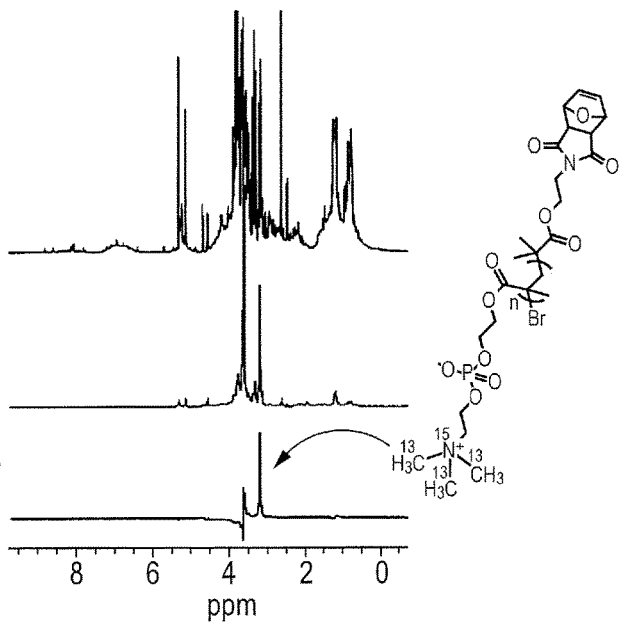
FIG. 13A
FIG. 13B
FIG. 13C
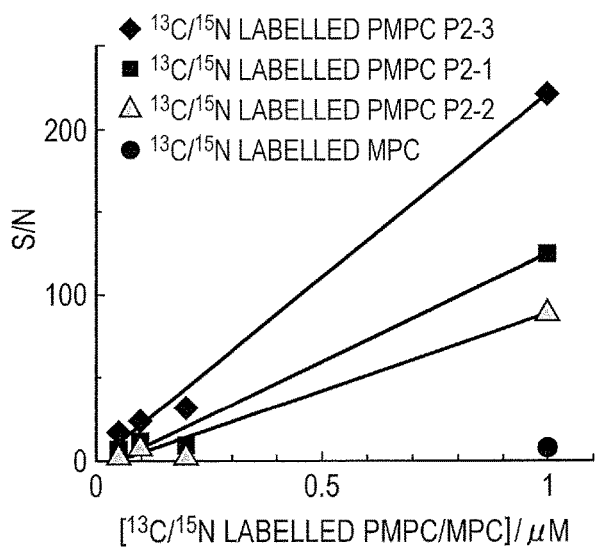
FIG. 14A
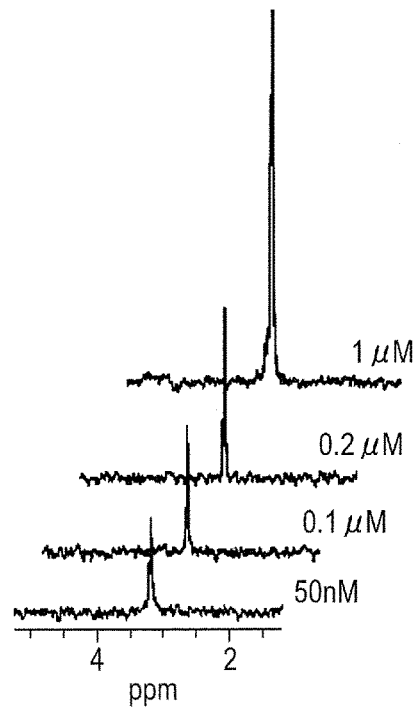
FIG. 14B

POLYMER, CONTRAST AGENT FOR NUCLEAR MAGNETIC RESONANCE ANALYSIS OR MAGNETIC RESONANCE IMAGING USING THE POLYMER, COMPOUND AND METHOD OF NUCLEAR MAGNETIC RESONANCE ANALYSIS AND METHOD OF MAGNETIC RESONANCE IMAGING USING THE POLYMER

TECHNICAL FIELD

The present invention relates to a polymer, a contrast agent for nuclear magnetic resonance analysis or magnetic resonance imaging using the polymer, a compound, and a method of nuclear magnetic resonance analysis and a method of magnetic resonance imaging using the polymer.

BACKGROUND ART

Magnetic resonance imaging (hereinafter sometimes abbreviated as MRI), that is, an imaging method based on the principle of nuclear magnetic resonance (NMR), is widely employed in medical settings because this method is only mildly invasive, has high spatial resolution and is excellent for examining morphologies. In general, MRI images (not spectra) are obtained based on a difference in relaxation time and are generically used because of the problem of background noise caused by the approximately 60% of water and lipid in a living body.

In general, $^1$H NMR, $^1$H is irradiated with pulses, so as to detect an NMR signal therefrom. In contrast, in multiple resonance NMR, an NMR signal is detected by utilizing magnetization coherence transfer of the NMR signal of $^1$H to an adjacent NMR active nucleus, and by this method, a specific chemical bond, such as a $^1$H—$^{13}$C, a $^1$H—$^{13}$C—$^{15}$N sequence or a $^1$H—$^{13}$C—$^{13}$C sequence, can be selectively detected. Here, $^{13}$C and $^{15}$N are stable isotopes of $^{12}$C and $^{14}$N, respectively.

If a $^1$H—$^{13}$C sequence is to be selectively detected, the magnetization transfers from $^1$H to $^{13}$C and then back to $^1$H, and thus, the proton in the $^1$H—$^{13}$C sequence can be detected. Alternatively, if a $^1$H—$^{13}$C—$^{15}$N sequence is to be selectively detected, the magnetization transfers from $^1$H through $^{13}$C to $^{15}$N and then back through $^{13}$C to $^1$H, and thus, the proton in the $^1$H—$^{13}$C—$^{15}$N sequence can be detected. This method is largely characterized by low natural abundances of these sequences. For example, the natural abundance of $^1$H—$^{13}$C—$^{15}$N is as low as 0.0040% (because the natural abundances of $^{13}$C and $^{15}$N are 1.1% and 0.37%, respectively), and therefore, background noise that causes a problem in conventional magnetic resonance imaging is largely suppressed. Consequently, a compound containing a sequence of $^1$H—$^{13}$C—$^{15}$N or the like shows high selectivity and high sensitivity as a contrast agent for nuclear magnetic resonance analysis or magnetic resonance imaging.

PTL 1 discloses the following: A choline chloride labeled with $^{13}$C and $^{15}$N is administered to a tumor-bearing mouse through a tail vein. The liver, kidney and tumor extracted from the mouse 1 h after the administration are ground, and the resultant mixture is subjected to centrifugal separation for removing impurities. When the thus obtained supernatant solution is analyzed by $^1$H—{$^{13}$C—$^{15}$N} triple resonance NMR, a $^1$H signal derived from a methyl group of choline at 3.0 ppm can be detected.

CITATION LIST

Patent Literature

PTL 1: Japanese Patent Application Laid-Open No. 2009-79046

SUMMARY OF THE INVENTION

Technical Problem

The choline chloride labeled with $^{13}$C and $^{15}$N disclosed in PTL 1 has nine $^1$H—$^{13}$C—$^{15}$N sequences in one molecule. If the number of $^1$H—$^{13}$C—$^{15}$N sequences, $^1$H—$^{15}$N—$^{13}$C sequences or $^1$H—$^{13}$C—$^{13}$C sequences in one molecule is further increased, the abundance of such sequences in a contrast agent can be increased, so that the nuclear magnetic resonance analysis and the magnetic resonance imaging can be conducted with higher selectivity and higher sensitivity.

The present invention was achieved in consideration of such a problem, and an object of the present invention is to provide a novel polymer showing high selectivity and high sensitivity in a method of nuclear magnetic resonance analysis or a method of magnetic resonance imaging and a contrast agent including the polymer for use in nuclear magnetic resonance analysis or magnetic resonance imaging.

Solution to the Problem

A polymer of the present invention is a polymer including, in a main chain, one or a plurality of repeating unit(s) selected from the group consisting of the following Formulas (x1) to (x3) and having a degree of polymerization of two or more and 5000 or less, wherein a side chain of each of the repeating unit(s) has a structure selected from the group consisting of the following Formulas (y1) to (y3):

(x1)

(x2)

(x3)

(y1)

(y2)

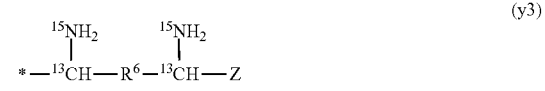

(y3)

wherein in Formulas (x1) to (x3) above, each of $R^1$ to $R^4$ independently represents a hydrogen atom, or a substituted or unsubstituted hydrocarbon group having one or more and four or less carbon atoms; $R^5$ represents a substituted or unsubstituted hydrocarbon group having one or more and nine or less carbon atoms, and if $R^5$ is a hydrocarbon group having two or more carbon atoms, any of the carbon atoms may be bound to the side chain, in Formulas (x1) to (x3) above, the symbol * (an asterisk) represents a bond to the side chain directly or via a linker, in Formulas (y1) to (y3) above, the symbol * (an asterisk) represents a bond to the main chain directly or via a linker, in Formulas (y1) to (y3) above, Z represents an arbitrary monovalent atom or monovalent atom group, in Formula (y3) above, $R^6$ represents a direct bond, or a substituted or unsubstituted hydrocarbon group having one or more and four or less carbon atoms, and a substituent of each of $R^1$ to $R^6$ is a functional group including at least one selected from the group consisting of a halogen atom, an oxygen atom and a nitrogen atom.

A compound of the present invention is represented by any one of the following Formulas (j1) to (j12)

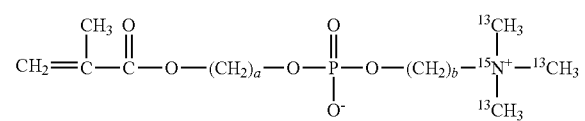
(j1)

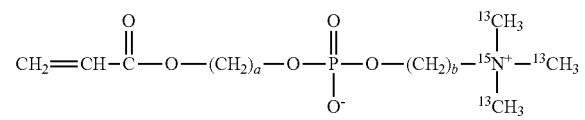
(j2)

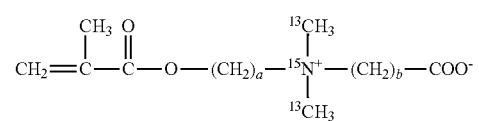
(j3)

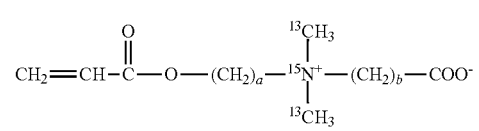
(j4)

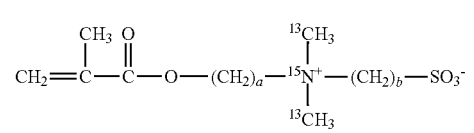
(j5)

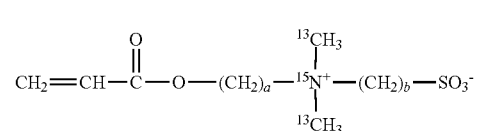
(j6)

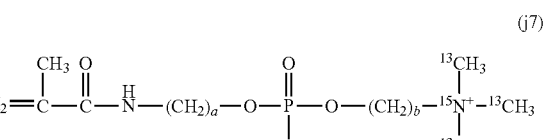
(j7)

-continued

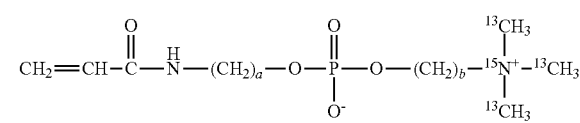
(j8)

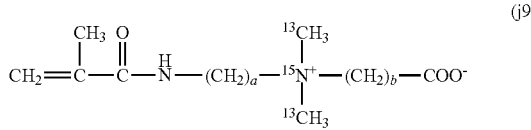
(j9)

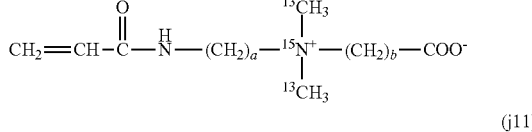
(j10)

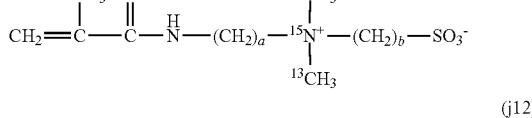
(j11)

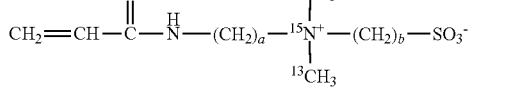
(j12)

wherein, in Formulas (j1) to (j12) above, each of a and b independently represents an integer of one or more and four or less, and a hydrogen atom of a methylene group is optionally replaced by another atom.

A method of nuclear magnetic resonance analysis of the present invention, including detecting a polymer in a specimen, includes: preparing the polymer; providing the polymer to the specimen; and applying electromagnetic waves to the specimen provided with the polymer, wherein magnetization transfer (coherence transfer) among nuclei in a $^1H$—$^{13}C$—$^{15}N$ bond sequence, a $^1H$—$^{15}N$—$^{13}C$ bond sequence or a $^1H$—$^{13}C$—$^{13}C$ bond sequence of the polymer is utilized for detecting the polymer.

A method of magnetic resonance imaging of the present invention, including detecting the position of a polymer in a specimen, includes: preparing the polymer; providing the polymer to the specimen; and applying electromagnetic waves to the specimen provided with the polymer, wherein magnetization transfer (coherence transfer) among nuclei in a $^1H$—$^{13}C$—$^{15}N$ bond sequence, a $^1H$—$^{15}N$—$^{13}C$ bond sequence or a $^1H$—$^{13}C$—$^{13}C$ bond sequence of the polymer is utilized for detecting the position of the polymer.

Advantageous Effects of the Invention

Using a polymer of the present invention, because the polymer includes, in side chains thereof, a large number of sequences of $^1H$—$^{13}C$—$^{15}N$, $^1H$—$^{15}N$—$^{13}C$ or $^1H$—$^{13}C$—$^{13}C$, that is, a structure labeled with the stable isotopes $^{13}C$ and $^{15}N$, the abundance of such a sequence in one molecule can be increased, so that high selectivity and higher sensitivity can be attained.

Further features of the present invention will become apparent from the following description of exemplary embodiments with reference to the attached drawings.

BRIEF DESCRIPTION OF DRAWINGS

FIG. 13A is a $^1$H NMR spectrum of the $^{13}$C/$^{15}$N labeled PMPC p2-3 in a mouse liver extract.

FIG. 13B is a $^1$H—{$^{13}$C} double resonance NMR spectrum of the $^{13}$C/$^{15}$N labeled PMPC p2-3 in a mouse liver extract.

FIG. 13C is a $^1$H—{$^{13}$C—$^{15}$N} triple resonance NMR spectrum of the $^{13}$C/$^{15}$N labeled PMPC p2-3 in a mouse liver extract.

FIGS. 14A and 14B show a macromolecular effect (effect of accumulation of stable isotopes) on $^1$H—{$^{13}$C—$^{15}$N} triple resonance signal sensitivity.

DESCRIPTION OF EMBODIMENT

Figure 1:
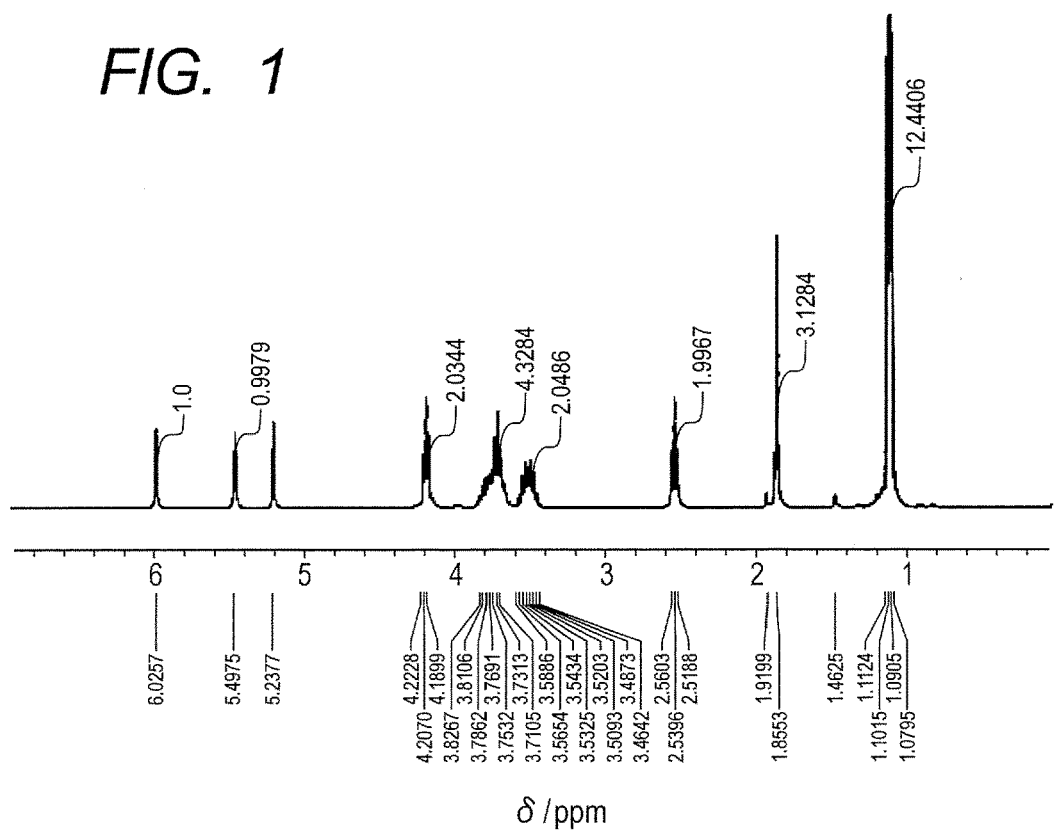
FIG. 1 is a $^1H$ NMR spectrum of 2-((2-cyanoethoxy)(diisopropylamino)phosphinooxy)ethyl methacrylate (Formula (m6)).

A contrast agent according to the present invention includes a polymer, and the polymer has, in side chains thereof, one or a plurality of sequences selected from the group consisting of a $^1$H—$^{13}$C—$^{15}$N sequence, a $^1$H—$^{15}$N—$^{13}$C sequence and a $^1$H—$^{13}$C—$^{13}$C sequence that are detectable by the principle of nuclear magnetic resonance. These sequences are detected based on similar principles, and for example, a $^1$H—$^{13}$C—$^{15}$N sequence can be detected by transferring the magnetization of $^1$H to $^{13}$C, transferring the magnetization of $^{13}$C to $^{15}$N, returning the magnetization of $^{15}$N to $^{13}$C, and returning the magnetization of $^{13}$C to $^1$H. Similarly, a $^1$H—$^{15}$N—$^{13}$C sequence can be detected by transferring the magnetization of $^1$H to $^{15}$N, transferring the magnetization of $^{15}$N to $^{13}$C, returning the magnetization of $^{13}$C to $^{15}$N and returning the magnetization of $^{15}$N to $^1$H. In addition, a $^1$H—$^{13}$C—$^{13}$C sequence can be similarly detected. The contrast agent including the polymer having such a structure permits nuclear magnetic resonance analysis and magnetic resonance imaging with higher selectivity and higher sensitivity because a large number of such sequences detectable by the principle of nuclear magnetic resonance are included in the side chains. It is noted that a plurality of the above sequences can be included per side chain unit.

Because $^{15}$N and $^{13}$C used in these sequences are stable isotopes, there is no danger of exposure and no restriction in handling time as compared with conventional labeled compounds using radioactive isotopes.

An embodiment of the present invention will now be described; however, the present invention is not limited to the embodiment.

(Polymer)

A side chain of a polymer of the present embodiment has a structure selected from the group consisting of the following Formulas (y1) to (y3).

(y1)

(y2)

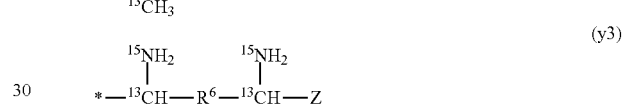

(y3)

In Formulas (y1) to (y3) above, the symbol * (an asterisk) represents a bond to a main chain directly or via a linker. In Formulas (y1) to (y3) above, Z represents an arbitrary monovalent atom or monovalent atom group.

In Formula (y3) above, $R^6$ represents a direct bond, or a substituted or unsubstituted hydrocarbon group having one or more and four or less carbon atoms. A substituent of $R^6$ is a functional group including at least one selected from the group consisting of a halogen atom, an oxygen atom and a nitrogen atom.

As described above, because a side chain of the polymer of the present embodiment includes at least one of the structures of Formulas (y1) to (y3), namely, the sequence of $^1$H—$^{13}$C—$^{15}$N, $^1$H—$^{15}$N—$^{13}$C or $^1$H—$^{13}$C—$^{13}$C, the polymer can be used as a contrast agent with high selectivity in the method of nuclear magnetic resonance analysis or the method of magnetic resonance imaging. Furthermore, because many of such sequences are included, the polymer can be used as a highly sensitive contrast agent in the method of nuclear magnetic resonance analysis or the method of magnetic resonance imaging. The polymer may include one or more of these sequences and preferably includes at least the $^1$H—$^{13}$C—$^{15}$N sequence.

In the polymer of the present embodiment, the linker and the side chain can be selected from the group consisting of the following Formulas (y5) to (y7).

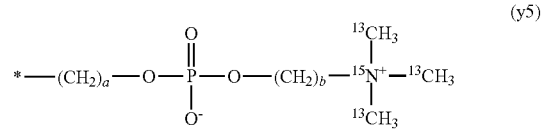

(y5)

-continued

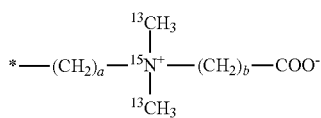
(y6)

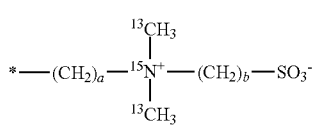
(y7)

In Formulas (y5) to (y7) above, the symbol * (an asterisk) represents a bond to the main chain.

In Formulas (y5) to (y7) above, each of a and b independently represents an integer of one or more and four or less, and a hydrogen atom of a methylene group of the above formulas is optionally replaced by another atom.

If a structure similar to choline is included as in Formula (y5) above, the polymer of the present embodiment is evidence of high tumor accumulation. Alternatively, if a carboxyl group is included as in Formula (y6) above, the structure is preferable because the carboxyl group can be easily bound to a trapping molecule that specifically binds to a target site such as an antibody. Alternatively, if a sulfonic group is included as in Formula (y7) above, the structure is preferable because the structure is highly hydrophilic and minimally aggregates in an organism.

(Main Chain)

The polymer of the present embodiment can include, as a main chain, a repeating unit represented by any one of the following Formulas (x1) to (x3).

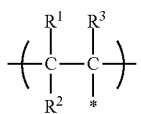
(x1)

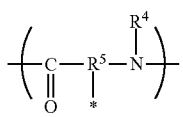
(x2)

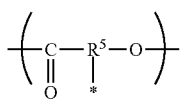
(x3)

In Formulas (x1) to (x3) above, each of $R^1$ to $R^4$ independently represents a hydrogen atom, or a substituted or unsubstituted hydrocarbon group having one or more and four or less carbon atoms, and $R^5$ represents a substituted or unsubstituted hydrocarbon group having one or more and nine or less carbon atoms. If $R^5$ is a hydrocarbon group having two or more carbon atoms, any of the carbon atoms may be bound to the side chain. A substituent of each of $R^1$ to $R^5$ is a functional group including at least one selected from the group consisting of a halogen atom, an oxygen atom and a nitrogen atom.

In Formulas (x1) to (x3) above, the symbol * (an asterisk) represents a bond to the side chain directly or via a linker.

The polymer of the present embodiment has a degree of polymerization of preferably two or more and 5000 or less.

In addition, the degree of polymerization of the polymer of the present embodiment is preferably 10 or more and more preferably 20 or more. If the degree of polymerization is 10 or more, the sensitivity is high, and if the degree of polymerization is 20 or more, the sensitivity is even higher.

The degree of polymerization of the polymer of the present embodiment is preferably 1000 or less and more preferably 400 or less. If the degree of polymerization is 1000 or less, the viscosity is low, which is preferable in administering the polymer of the present embodiment to an organism. The degree of polymerization of the polymer of the present embodiment is preferably 10 or more and 1000 or less, more preferably 10 or more and 400 or less, and still more preferably 20 or more and 400 or less.

The main chain may be in the form of a straight chain or may have a branched structure.

The repeating unit of the main chain may include one repeating unit or two or more repeating units.

(Exemplary Embodiment of Polymer)

In the polymer of the present embodiment, the repeating unit of the main chain can include merely the repeating units of the above Formulas (x1) to (x3). In this case, a structure including the repeating unit is represented by the following Formula (I).

(I)

In Formula (I) above, X represents any one of the following Formulas (x1) to (x3), and the polymer has a degree of polymerization of two or more and 5000 or less. In the following Formulas (x1) to (x3), the symbol * (an asterisk) represents a bond to L of the above Formula (I) or a bond to Y when L represents a direct bond. In the following Formulas (x1) to (x3), each of $R^1$ to $R^4$ independently represents a hydrogen atom, or a substituted or unsubstituted hydrocarbon group having one or more and four or less carbon atoms, and $R^5$ represents a substituted or unsubstituted hydrocarbon group having one or more and nine or less carbon atoms. A substituent of $R^1$ to $R^5$ is a functional group including at least one selected from the group consisting of a halogen atom, an oxygen atom and a nitrogen atom.

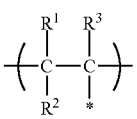
(x1)

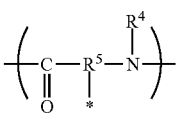
(x2)

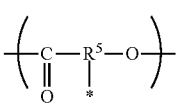
(x3)

In Formula (I) above, L is a direct bond or an arbitrary divalent atom or divalent atom group. If L is an arbitrary divalent atom or divalent atom group, L binds to X or Y of Formula (I) above.

In Formula (I) above, Y is represented by any one of Formulas (y1) to (y3) below. In the following Formulas (y1) to (y3), the symbol * (an asterisk) represents a bond to L of Formula (I) above or a bond to X if L is a direct bond, and Z represents an arbitrary monovalent atom or monovalent atom group. In the following Formula (y3), $R^6$ represents a direct bond, or a substituted or unsubstituted hydrocarbon group having one or more and four or less carbon atoms. A substituent of $R^6$ is a functional group including at least one selected from the group consisting of a halogen atom, an oxygen atom and a nitrogen atom.

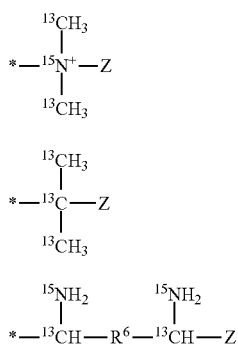

(y1)

(y2)

(y3)

Furthermore, in the polymer of the present embodiment, L of Formula (I) can be selected from the group consisting of a substituted or unsubstituted hydrocarbon group having one or more and four or less carbon atoms and the following Formulas (l1) to (l3).

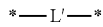 (l1)

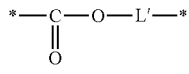 (l2)

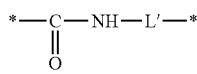 (l3)

A substituent of the hydrocarbon group is a functional group including at least one selected from the group consisting of a halogen atom, an oxygen atom and a nitrogen atom.

In Formulas (l1) to (l3) above, the symbol * (an asterisk) represents a bond to X or Y of Formula (I).

In Formulas (l1) to (l3) above, L' is selected from the group consisting of a substituted or unsubstituted hydrocarbon group having one or more and four or less carbon atoms and the following Formula (l').

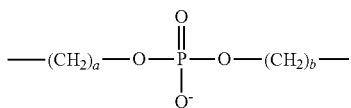

(l')

In Formula (l') above, each of a and b independently represents an integer of one or more and four or less, and the hydrocarbon group having one or more and four or less carbon atoms of L' and a hydrogen atom of a methylene group of Formula (l') is optionally replaced by another atom such as a halogen atom, an oxygen atom or a nitrogen atom.

Furthermore, in the polymer of the present embodiment, Z of Formula (y1) or (y2) can be represented by the following Formula (z1), or Z of Formulas (y1) to (y3) can be represented by the following Formula (z2) because high sensitivity may be thus attained.

 (z1)

 (z2)

In Formulas (z1) and (z2) above, the symbol * (an asterisk) represents a bond to $^{13}C$ or $^{15}N$ of Formulas (y1) to (y3).

In the polymer of the present embodiment, if Z of Formulas (y1) to (y3) is represented by Formula (z3) or (z4) below, the polymer is preferred because the polymer can be easily bound to an antibody and is highly hydrophilic.

 (z3)

 (z4)

In Formulas (z3) and (z4) above, the symbol * (an asterisk) represents a bond to $^{13}C$ or $^{15}N$ of Formulas (y1) to (y3). In Formulas (z3) and (z4) above, d represents an integer of one or more and four or less, and a hydrogen atom of a methylene group is optionally replaced by another atom such as a halogen atom, an oxygen atom or a nitrogen atom.

If the above Formula (z2) forms a structure similar to choline, the polymer of the present embodiment is able to show high tumor accumulation. If a carboxyl group is included as in Formula (z3) above, the structure is preferable because the carboxyl group can be easily bound to a trapping molecule that specifically binds to a target site such as an antibody. Alternatively, if a sulfonic group is included as in Formula (z4) above, the structure is preferable because the polymer is highly hydrophilic and minimally aggregates in an organism.

Examples of the polymer of the present embodiment include the following Formulas (i1) to (i12).

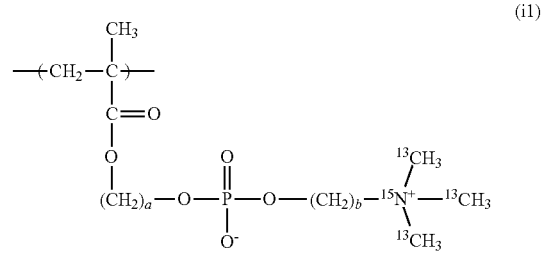 (i1)

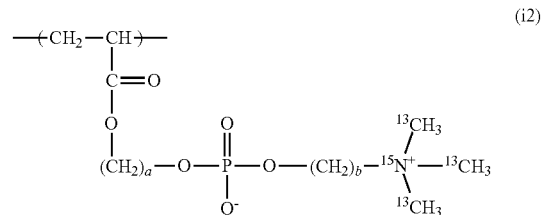 (i2)

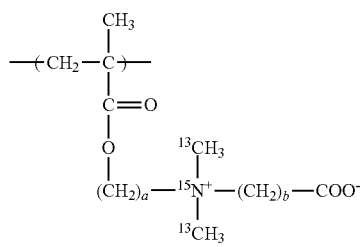
(i3)

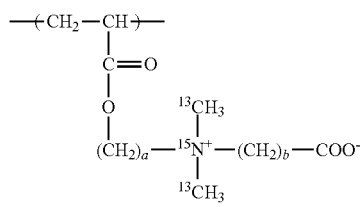
(i4)

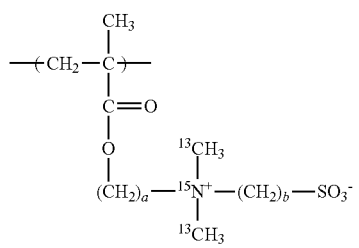
(i5)

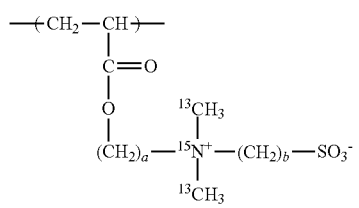
(i6)

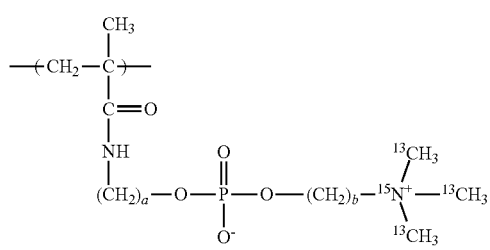
(i7)

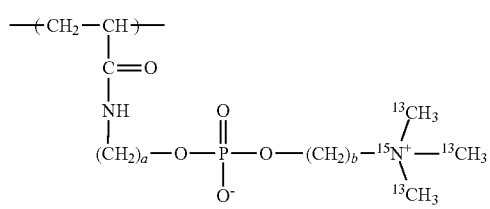
(i8)

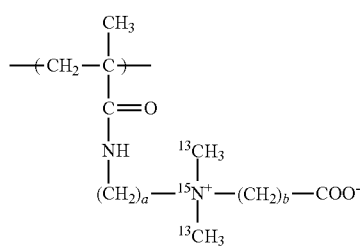
(i9)

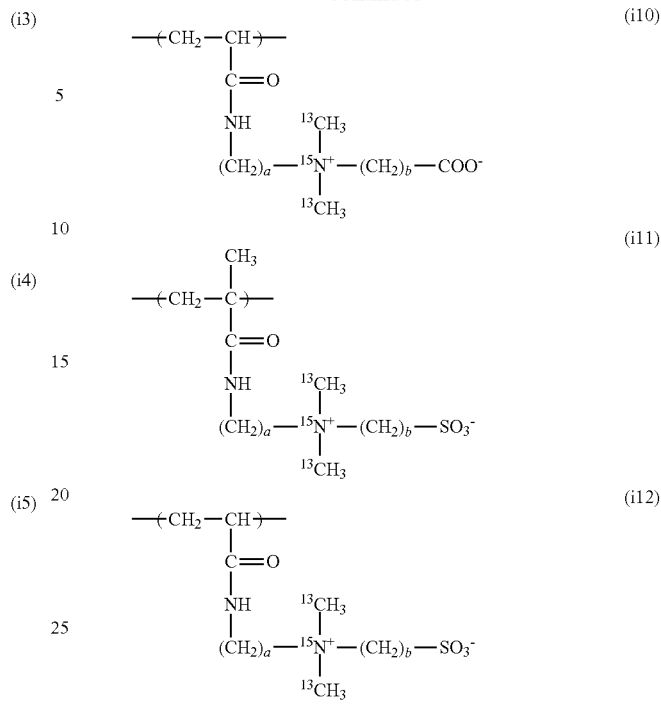

In Formulas (i1) to (i12) above, each of a and b independently represents an integer of one or more and four or less, and a hydrogen atom of a methylene group is optionally replaced by another atom.

Incidentally, the polymer of the present embodiment is hereinafter sometimes designated as the $^{13}C/^{15}N$ labeled polymer ($^{13}C/^{15}N$-PMPC).

(Trapping Molecule)

The polymer of the present embodiment can include a trapping molecule that specifically binds to a target site. Examples of a trapping molecule that specifically binds to a target site include a substance that specifically binds to a target site of a tumor or the like, and a substance that specifically binds to a substance present around a target site, and the trapping molecule may be selected freely from chemical substances including biomolecules and medicines. Specific examples of the trapping molecule include antibodies, antibody fragments, enzymes, biologically active peptides, glycopeptides, sugar chains, lipids, nucleic acids and molecular recognition compounds. One of these substances may be used singly, or a plurality of the substances may be used in combination. When the polymer of the present embodiment including a chemically bound trapping molecule is used, a specific target site can be detected, or dynamics, localization, drug effects, metabolism or the like of a target substance can be traced.

Here, an antibody is a general term for proteins belonging to the immunoglobulin family induced by an immune system in response to a specific molecule (antigen), and has the property of binding to the antigen. An example of the immunoglobulin family includes immunoglobulin G (hereinafter sometimes abbreviated as IgG). Here, the antibody may be a polyclonal antibody or a monoclonal antibody. Incidentally, an antibody portion may include, apart from an antibody, any amino acid as long as the antigen-binding capacity is not harmed.

The antibody is not limited to a whole antibody but may be an antibody fragment. An antibody fragment means a derivative of an antibody obtained by reducing the molecular weight with the property of binding to a specific molecule retained. Examples of an antibody fragment include a Fab fragment, a Fab' fragment, a F(ab')2, polypeptide including a variable heavy chain (VH) domain alone, a variable light chain (VL) domain alone, a composite of VH and VL, a camelized VH domain or a complementary determining region (CDR) of an antibody, and a single chain antibody (single chain Fv, hereinafter sometimes abbreviated as scFv) that is a polypeptide including a VH region and a VL region of an antibody linked with peptide linker. Because an antibody fragment has a smaller molecular size than a whole antibody, an antibody fragment has high tissue permeability and a high clearance rate, and hence is suitable for use in a diagnostic agent or a contrast agent.

Of antibody fragments, a single chain antibody is preferred. This is because a single chain antibody can be inexpensively and easily prepared corresponding to each of various antigens, and has a smaller molecular weight than whole antibodies and antibody fragments other than the single chain antibody, and hence is rapidly removed from a body or easily reaches a lesion site. Consequently, a single chain antibody is suitable for use in detecting or treating a lesion site.

A method for binding a trapping molecule to the polymer of the present embodiment depends upon the type of trapping molecule to be used, but any of the known methods can be employed. For example, a method in which a reaction is caused between a functional group at an end of the polymer of the present embodiment and a functional group of the trapping molecule for attaining a chemical bond can be employed.

If the functional group at an end of the polymer of the present embodiment is a maleimide group, a target substance can be obtained by causing a reaction with a trapping molecule having a thiol group. Alternatively, if the functional group at an end of the polymer of the present embodiment is an N-hydroxysuccinimide group, a target substance can be obtained by causing a reaction with a trapping molecule having an amino group. After the reaction, the polymer having the trapping molecule bound thereto can be separated and purified.

(Copolymer)

The polymer of the present embodiment may be a copolymer having two or more repeating units. If the polymer of the present embodiment is a copolymer, the copolymer may be any one of an alternating copolymer, a random copolymer and a block copolymer.

If the polymer of the present embodiment is a copolymer, the copolymer may include, apart from the aforementioned repeating unit(s) included in the main chain, a repeating unit derived from a methacrylate monomer, a repeating unit derived from a methacrylamide monomer, a repeating unit derived from an amino acid monomer or a repeating unit derived from a hydroxy acid monomer.

If the polymer of the present embodiment is a copolymer, the copolymer may include, apart from the aforementioned repeating unit(s) included in the main chain, a repeating unit not having the side chain of the present embodiment but represented by any one of the following Formulas (a1) to (a3).

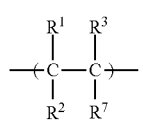

(a1)

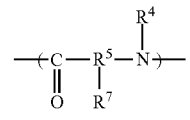

(a2)

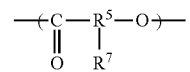

(a3)

In Formulas (a1) to (a3) above, $R^7$ represents an arbitrary monovalent atom or monovalent atom group and is a hydrogen atom or preferably a substituted or unsubstituted hydrocarbon group having one or more and six or less carbon atoms. A substituent of $R^7$ is a functional group including at least one selected from the group consisting of a halogen atom, an oxygen atom and a nitrogen atom.

Incidentally, in the case where the polymer of the present embodiment is a copolymer, all repeating units included in the copolymer may have, in side chains thereof, the structures represented by Formulas (y1) to (y3) described above, or merely some of the repeating units included in the copolymer may have the structures represented by Formulas (y1) to (y3) described above. In the former case, extremely high sensitivity can be attained when the copolymer is used as a contrast agent for the multiple resonance NMR. On the other hand, in the latter case, because a repeating unit having none of the structures represented by the above Formulas (y1) to (y3) is used, the copolymer can be designed according to a purpose; for example, to modify the hydrophilic property or absorption ability in an organism.

(Polymer End)

The end of the repeating unit of the polymer of the present embodiment is not especially limited but preferably includes any one of an N-hydroxysuccinimide group, a maleimide group, an amino group, an azide group, an ethynyl group, a vinyl group, a trichlorosilyl group, a thiol group, a hydroxyl group and an alkyl group. Such a functional group can be easily bound to a trapping molecule that specifically binds to a target site such as an antibody. The end of the polymer of the present embodiment has, for example, any one of the structures of the following Formulas (b1) to (b9).

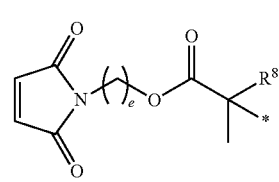

(b1)

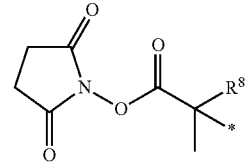

(b2)

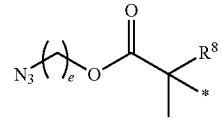

(b3)

-continued (b4) 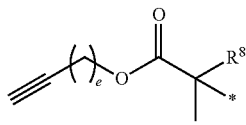

(b5) 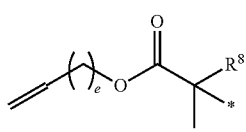

(b6) 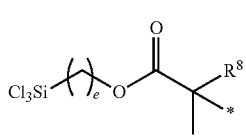

(b7) 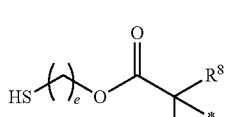

(b8) 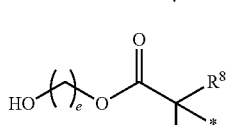

(b9) 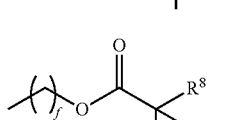

In Formulas (b1) to (b9) above, e represents an integer of one or more and 11 or less, f represents an integer of zero or more and 17 or less, and $R^8$ represents a hydrogen atom or a methyl group. Both ends of the polymer of the present embodiment may have the same structure or different structures. In Formulas (b1) to (b9) above, the symbol * (an asterisk) represents a bond to a repeating unit of the main chain.

(Contrast Agent for Nuclear Magnetic Resonance Analysis or Magnetic Resonance Imaging)

A contrast agent for nuclear magnetic resonance analysis or magnetic resonance imaging of the present embodiment includes the aforementioned polymer and a dispersion medium. Here, a dispersion medium is a liquid substance for dissolving the above polymer therein, and examples include a physiological saline solution, distilled water for injection and a phosphate buffer solution (PBS). Furthermore, in addition to the dispersion medium, the contrast agent may include a pharmacologically acceptable additive if necessary. In the contrast agent for the nuclear magnetic resonance analysis or the magnetic resonance imaging of the present embodiment, the above polymer may be previously dissolved in the dispersion medium, or the above polymer and the dispersion medium may be provided as a kit so that the polymer can be dissolved in the dispersion medium before administration to an organism. The contrast agent of the present embodiment can be accumulated in a larger amount in a tumor site than in a normal region within an organism owing to the enhanced permeability and retention (EPR) effect. By detecting the accumulated contrast agent by the method of nuclear magnetic resonance analysis or the method of magnetic resonance imaging, the presence of a tumor can be detected or a specific tumor site can be imaged.

(Compound)

The polymer of the present embodiment can be synthesized by polymerizing a polymerizable compound by a known method. The polymerizable compound may have the structures represented by Formulas (y1) to (y3) mentioned above, or alternatively, the structures represented by the above Formulas (y1) to (y3) may be added to the polymer by modifying a side chain after the polymerization. For example, the polymer can be synthesized by polymerizing compounds of the following Formulas (j1) to (j12).

(j1) 

(j2) 

(j3) 

(j4) 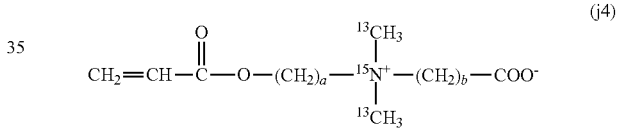

(j5) 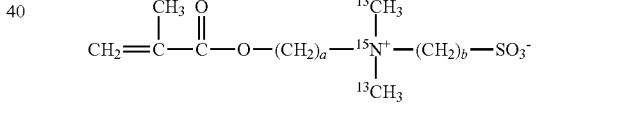

(j6) 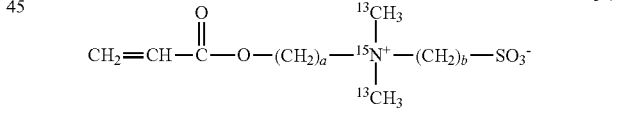

(j7) 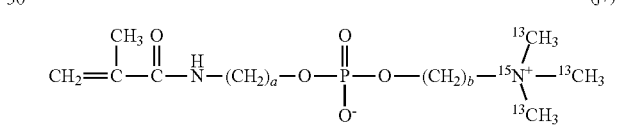

(j8) 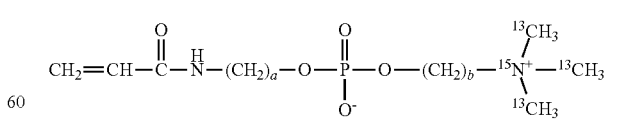

(j9) 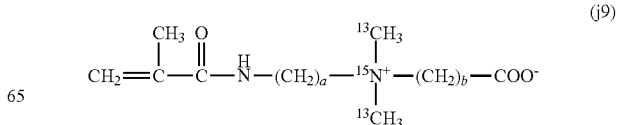

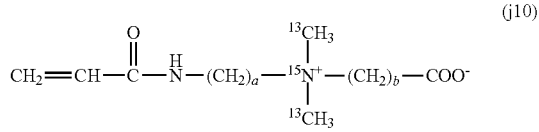
(j10)

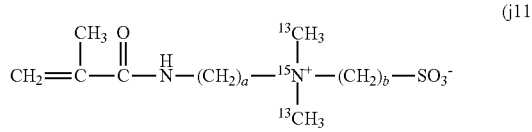
(j11)

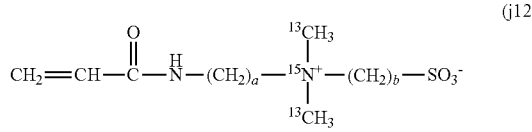
(j12)

In Formulas (j1) to (j12) above, each of a and b independently represents an integer of one or more and four or less, and a hydrogen atom of a methylene group is optionally replaced by another atom such as a halogen atom, an oxygen atom or a nitrogen atom. Incidentally, the compound of the present embodiment is hereinafter sometimes designated as the $^{13}C/^{15}N$ labeled monomer ($^{13}C/^{15}N$-MPC).

The polymer of the present embodiment mentioned above can be prepared by polymerizing these compounds.

(Polymerization of the Compound)

For the polymerization of the compound of the present embodiment, any of the conventionally known polymerization methods can be appropriately selected according to the type of compound.

If, for example, a vinyl monomer is selected as the above polymerizable compound, the living radical polymerization method, particularly the atom transfer radical polymerization (ATRP) method, may be employed as the polymerization method. Because the ATRP method is simple and the molecular weight can be easily controlled, the ATRP method is preferred.

If hydroxy acid or amino acid is selected as the polymerizable compound, condensation polymerization may be employed as the polymerization method. In employing condensation polymerization, a condensation agent may be appropriately used.

If lactide, lactone or lactam is selected as the polymerizable compound, ring-opening polymerization may be employed as the polymerization method. In employing the ring-opening polymerization, a catalyst may be appropriately used.

In the polymerization of the polymerizable compound, two or more compounds having different structures may be used for producing an alternating copolymer, a random copolymer or a block copolymer.

(Atom Transfer Radical Polymerization)

In the above ATRP method, a polymerization initiator having a highly reactive carbon-halogen bond and a transition metal complex working as a polymerization catalyst are used to polymerize a vinyl monomer.

The $^{13}C/^{15}N$ labeled polymer ($^{13}C/^{15}N$-PMPC) of the present embodiment can be obtained, for example, by the atom transfer radical polymerization as shown in the following Reaction Formula 1.

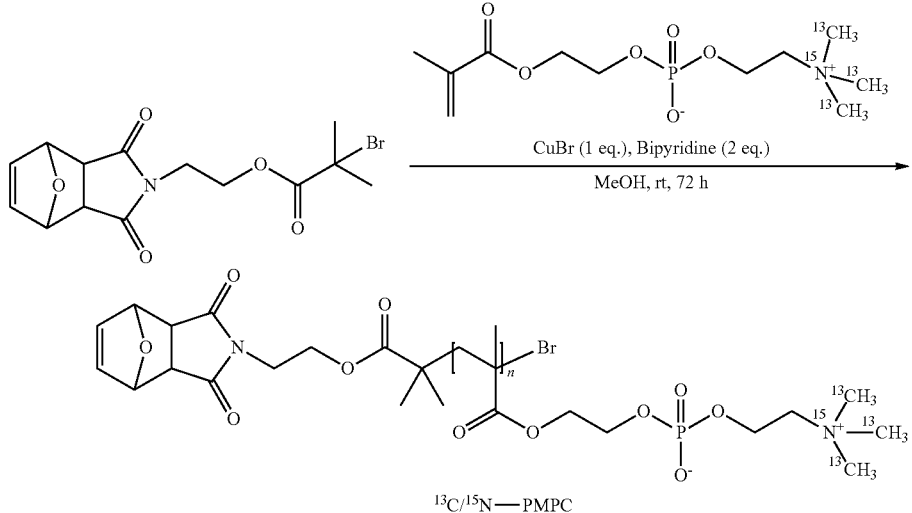
(Reaction Formula 1)

In the present embodiment, instead of producing a homopolymer, an alternating copolymer, a random copolymer or a block copolymer can be produced by using two or more vinyl monomers having different structures.

If a vinyl monomer is polymerized by the atom transfer radical polymerization, a polymerization initiator—for example, represented by any one of Formulas (k1) to (k9) below can be used. In the following Formulas (k1) to (k9), e represents an integer of 1 or more and 11 or less, f represents an integer of 0 or more and 17 or less, and $R^8$ represents a hydrogen atom or a methyl group.

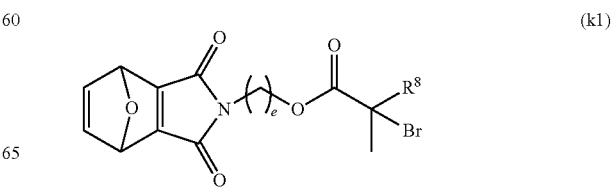
(k1)

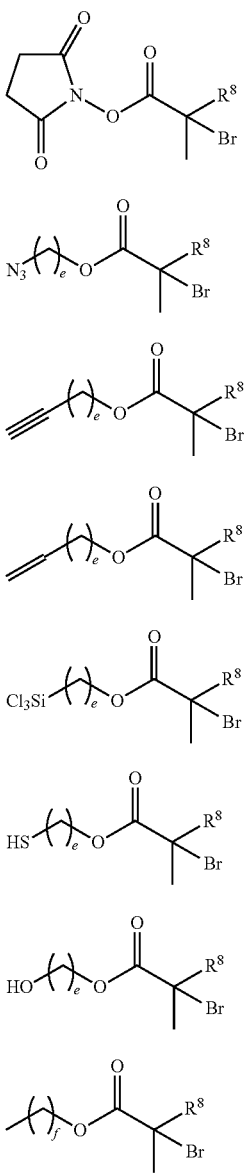

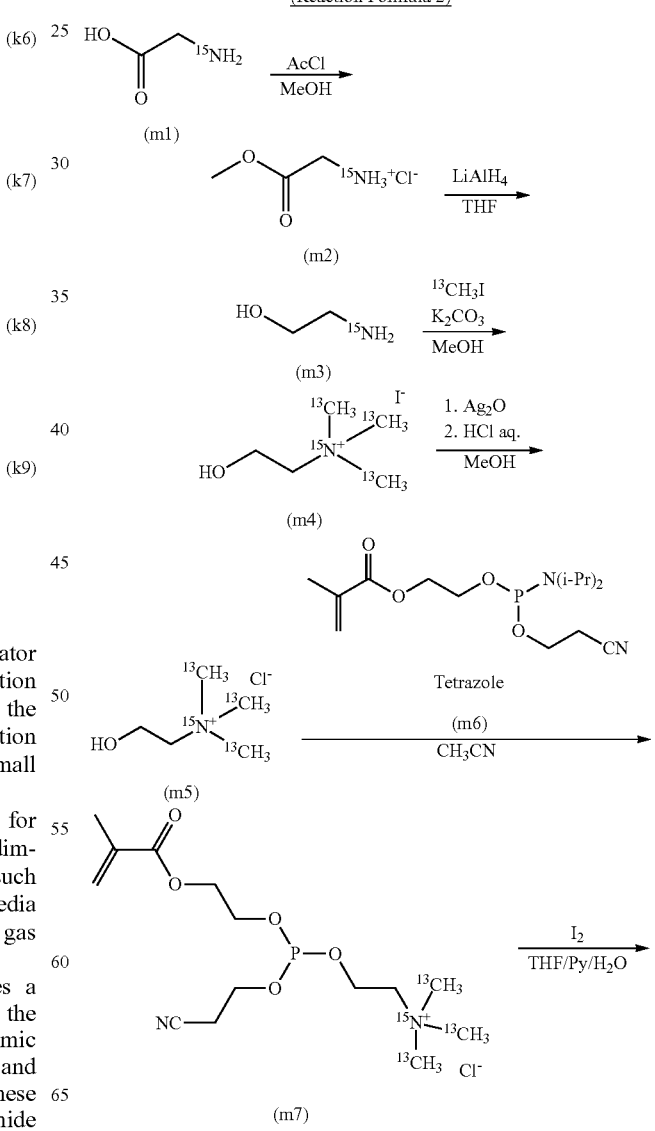

Under an inert gas atmosphere, a polymerization initiator and a transition metal complex are added to a reaction medium inducing a vinyl monomer, so as to conduct the atom transfer radical polymerization. The polymerization proceeds in a living manner, so that a polymer with a small molecular weight distribution can be obtained.

The reaction medium is not especially limited, but, for example, water, methanol, ethanol, dimethyl sulfoxide, dimethyl formamide and acetonitrile may be used. One such medium may be used singly or two or more of the media may be used in combination. As the inert gas, nitrogen gas or argon gas may be used.

The transition metal complex to be used includes a halogenated metal and a ligand. As metal species of the halogenated metal, transition metals from Ti with atomic number 22 to Zn with atomic number 30 are preferred, and Fe, Co, Ni and Cu are particularly preferred. Of these halogenated metals, cuprous chloride and cuprous bromide are preferred.

The ligand is not especially limited as long as the ligand can be coordinated in a halogenated metal, and for example, 2,2'-bipyridyl, tris(2-dimethylaminoethyl)amine, ethylenediamine, dimethylglyoxime, 1,4,8,11-tetramethyl-1,4,8,11-tetraazacyclotetradecane, 1,10-phenanthroline, N,N,N',N'',N''-pentamethyldiethylenetriamine, tris(2-aminoethyl)amine or the like can be used.

The polymerization temperature is in the range of 0° C. to 80° C., and preferably in the range of 10° C. to 60° C.

(Synthesis of Compound)

The compounds represented by Formulas (j1) to (j12) above can be synthesized by known methods. For example, the compound represented by the above Formula (j1) (wherein a=2 and b=2) can be synthesized according to Reaction Formula 2 below. To introduce a $^{13}C$ nucleus and a $^{15}N$ nucleus into 2-methacryloyloxyethyl phosphorylcholine (MPC), $^{15}N$ glycine represented by Formula (m1) is used as a starting material, and $^{13}C$ methyl iodide is used to introduce the $^{13}C$ nucleus. In this way, the targeted vinyl monomer ($^{13}C/^{15}N$-MPC) represented by Formula (j1) can be obtained in a yield of 48% (overall).

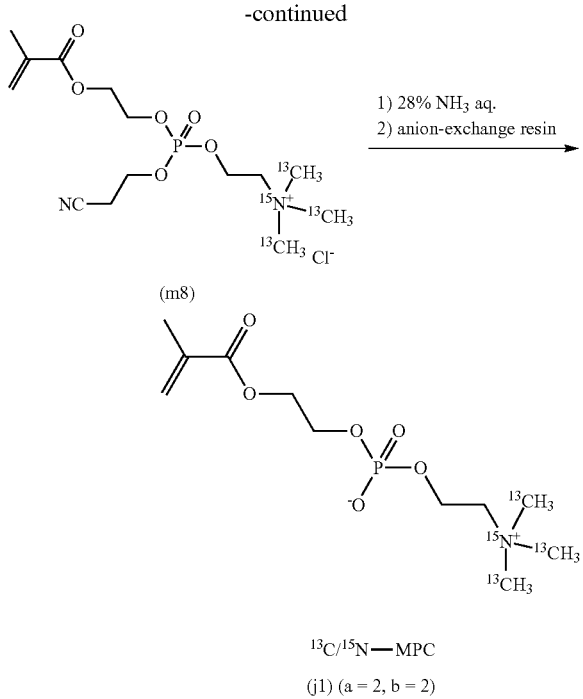

(j1) (a = 2, b = 2)

(Contrast Agent)

When the atom transfer radical polymerization is conducted using a polymerization initiator represented by any of Formulas (k1) to (k9) above and a $^{13}C/^{15}N$ labeled monomer, a polymer having a side chain double-labeled with stable isotopes of a $^{13}C$ nucleus and a $^{15}N$ nucleus can be obtained.

Onto the polymer obtained by the atom transfer radical polymerization using the polymerization initiator represented by any of Formulas (k1) to (k9) and the $^{13}C/^{15}N$ labeled monomer, a trapping molecule that specifically binds to a target site can be immobilized. However, in the case of Formula (k1), deprotection needs to be conducted for changing into a maleimide group.

(Method of Nuclear Magnetic Resonance Analysis)

A method of nuclear magnetic resonance analysis of the present embodiment includes detecting a polymer included in a specimen and further includes: preparing a $^{13}C/^{15}N$ labeled polymer corresponding to the polymer; providing the polymer to the specimen; and applying electromagnetic waves to the specimen provided with the polymer; and magnetization transfer (coherence transfer) among nuclei in a $^{1}H-^{13}C-^{15}N$ bond sequence, a $^{1}H-^{15}N-^{13}C$ bond sequence or a $^{1}H-^{13}C-^{13}C$ bond sequence of the polymer is utilized for detecting the polymer.

In the present embodiment, any one or more of these sequences may be used for detecting the polymer, and at least the $^{1}H-^{13}C-^{15}N$ sequence can be used.

(Method of Magnetic Resonance Imaging)

A method of magnetic resonance imaging of the present embodiment includes detecting the position of a polymer in a specimen and further includes: preparing a $^{13}C/^{15}N$ labeled polymer corresponding to the polymer; providing the polymer to the specimen; and applying electromagnetic waves to the specimen provided with the polymer; and magnetization transfer (coherence transfer) among nuclei in a $^{1}H-^{13}C-^{15}N$ bond sequence, a $^{1}H-^{15}N-^{13}C$ bond sequence or a $^{1}H-^{13}C-^{13}C$ bond sequence of the polymer is utilized for detecting the position of the polymer. In the present embodiment, any one or more of these sequences may be used for detecting the polymer, and at least the $^{1}H-^{13}C-^{15}N$ sequence can be used.

When a contrast agent in which a trapping molecule is bound is used in the method of magnetic resonance imaging, the position of a tumor or the like can be detected through the aforementioned steps.

In providing the polymer as described above, the method for administering the polymer of the present embodiment to an organism is not especially limited, and a method of injection, oral administration or the like can be employed.

Furthermore, in the case where the polymer is used in an organism, various specific target sites can be detected by appropriately selecting the trapping molecule. If, for example, a substance that binds to a specific tumor is used as the trapping molecule, the specific tumor can be detected. Alternatively, if a substance that binds to a specific living substance such as a protein or an enzyme present in a large amount around a specific disease site is used as the trapping molecule, the specific disease can be detected. Furthermore, the polymer of the present embodiment can be used for detecting a tumor owing to the EPR effect, even when the trapping molecule is not included.

EXAMPLES

Specific reagents, reaction conditions and the like employed in preparing a polymer of the present invention in each example will now be described, but the reagents, reaction conditions and the like can be changed or modified, and these changes and modifications are connoted in the present invention. Consequently, the examples described below are given for the purpose of assisting in the understanding of the present invention and are not intended to limit the scope of the present invention in any way.

(Method for Measuring the NMR Spectrum)

The $^{1}H$ NMR spectrum was measured using a JEOL EX400 (400 MHz, manufactured by JEOL Ltd.) or a JEOL AL300 (300 MHz, manufactured by JEOL Ltd.).

The $^{13}C$ NMR spectrum was measured using a JEOL EX400 (100 MHz, manufactured by JEOL Ltd.) or a JEOL AL300 (75 MHz, manufactured by JEOL Ltd.).

The $^{15}N$ NMR spectrum was measured using an ECX400P (40 MHz, manufactured by JEOL Ltd.). The $^{31}P$ NMR spectrum was measured using an ECX400P (160 MHz, manufactured by JEOL Ltd.).

(Method for Measuring the Molecular Weight)

The electrospray ionization time-of-flight mass (ESI-TOF MS) spectrum was measured using a micrOTOF focus-KE spectrometer (manufactured by Bruker Daltonics).

The molecular weight was measured by gel permeation chromatography (GPC) (ChromNAV, manufactured by JASCO Corporation).

(Method for Measuring Multiple Resonance NMR)

The $^{1}H-\{^{13}C\}$ double resonance NMR and the $^{1}H-\{^{13}C-^{15}N\}$ triple resonance NMR were measured using a Bruker Avance 700 (700 MHz, equipped with a 5 mm TCI cryoprobe, manufactured by Bruker Biospin).

Example 1

Synthesis of $^{13}C/^{15}N$ Labeled MPC

Synthesis of 2-((2-cyanoethoxy) (diisopropylamino) phosphinooxy)ethyl methacrylate (of Formula (m6))

A methacrylate represented by Formula (m6) was synthesized according to Reaction Formula 3.

(Reaction Formula 3)

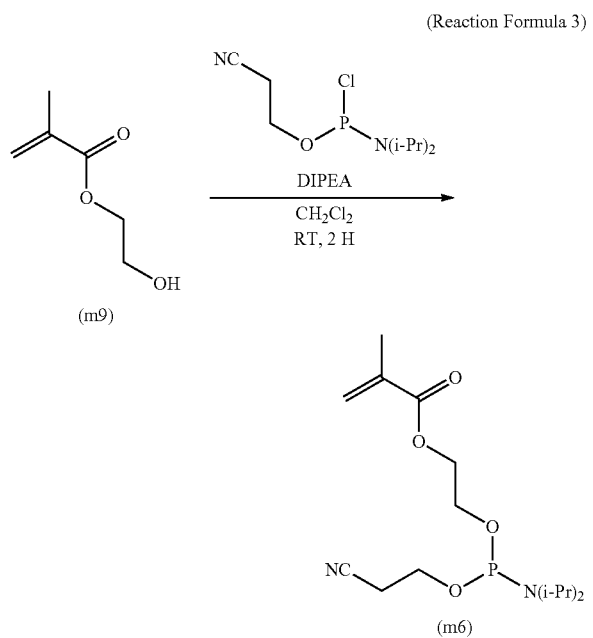

(m9)

(m6)

A 200 mL Pyrex (registered trademark) flask was charged with 2-hydroxyethylmethacrylate represented by Formula (m9) (0.65 mL, 5.4 mmol, manufactured by Aldrich) and dehydrated methylene chloride (DCM, manufactured by Kishida Chemical Co., Ltd.), followed by vacuum concentration. Subsequently, 15 mL of DCM, N,N-diisopropylethylamine (DIPEA) (3.5 mL, 20 mmol, manufactured by Aldrich) and 2-cyanoethyl-N,N-diisopropylchloro phosphoramidite (2.0 mL, 9.0 mmol, manufactured by Wako Pure Chemical Industries, Ltd.) were added thereto in this order with a syringe, and the resulting solution was stirred under an Ar atmosphere at 0° C. for 1 h. After diluting the reaction solution with DCM by approximately 20 times, saturated aqueous sodium bicarbonate was added thereto for extraction, and the resulting solution was dehydrated with anhydrous $MgSO_4$ (manufactured by Nacalai Tesque), followed by vacuum concentration with an evaporator. The residue was purified by silica gel column chromatography (hexane (manufactured by Nacalai Tesque):ethyl acetate (manufactured by Nacalai Tesque)=4:1), and thus, the methacrylate derivative represented by Formula (m6) (a colorless viscous liquid) was quantitatively obtained.

The $^1H$ NMR spectrum of Formula (m6) is illustrated in FIG. 1, and the spectrum data thereof are as follows:

$^1H$ NMR spectrum (300 MHz, $CD_2Cl_2$) δ/ppm=6.01-6.04 (1H, $CH_2$=C—), 5.48-5.51 (1H, $CH_2$=C—), 4.21 (t, J=4.94 Hz, 2H, —$CH_2$OCO), 3.67-3.87 (4H, —O$CH_2CH_2$—OP—, —PO$CH_2$—), 3.46-3.59 (2H, —NCH($CH_3$)$_3$), 2.54 (t, J=6.23 Hz, 2H, —$CH_2$CN), 1.86 (s, 3H, $CH_3$C=$CH_2$), 1.04-1.10 (12H, —NCH($CH_3$)$_2$)

Synthesis of $^{13}C/^{15}N$ Labeled MPC (of Formula (j1) (Wherein a=2 and b=2)

A $^{13}C/^{15}N$ labeled MPC represented by Formula (j1) (wherein a=2 and b=2) was synthesized according to Reaction Formula 4.

(Reaction Formula 4)

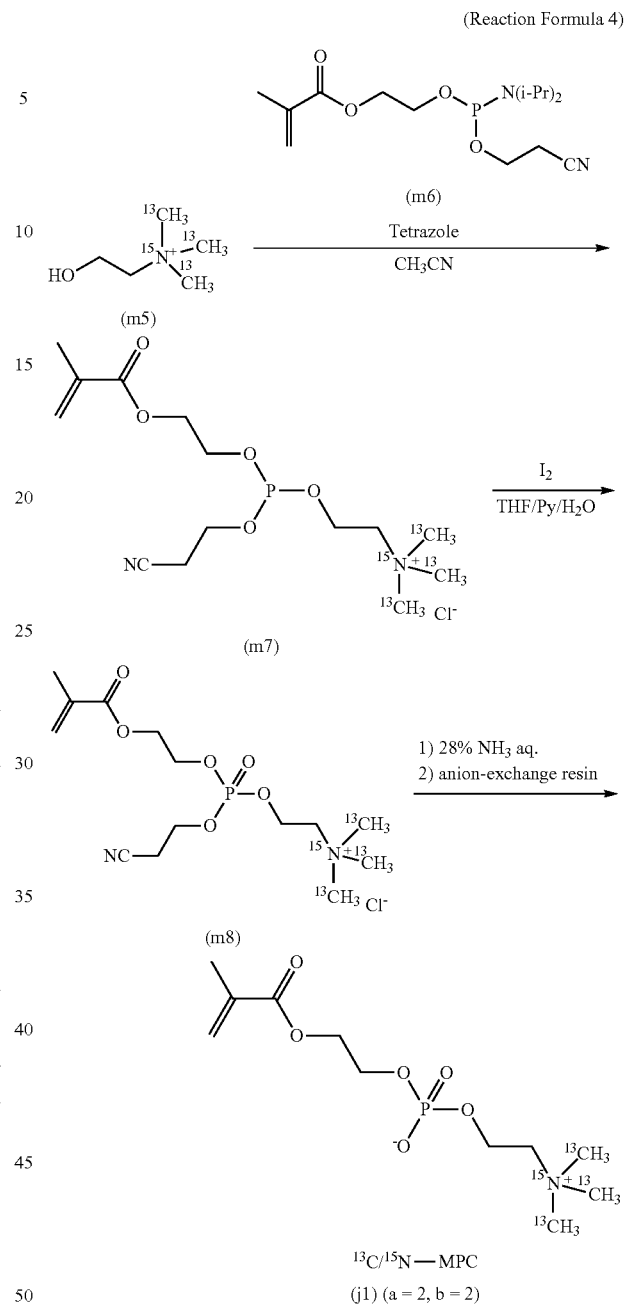

A 300 mL Pyrex (registered trademark) flask was charged with a compound represented by Formula (m5) (0.559 g, 3.91 mmol) and tetrazole (0.292 g, 4.12 mmol, manufactured by Nacalai Tesque), followed by vacuum drying. To the resultant mixture, a dehydrated acetonitrile solution (70 mL) of 50 mL of dehydrated acetonitrile (manufactured by Wako Pure Chemical Industries, Ltd.) and a compound represented by Formula (m6) (1.61 g, 4.88 mmol) were added with a syringe, and the resulting solution was stirred under an Ar atmosphere at room temperature for 14 h, so as to obtain a compound represented by Formula (m7) as a mixture (ESI-TOF MS m/z: 337.1652). Incidentally, the compound represented by Formula (m5) was prepared by a method described in PTL 1.

Subsequently, 60 mL of 0.1 M $I_2$ in THF/pyridine/water solution (manufactured by Glen Research) was added to the reaction solution, and the resulting solution was stirred at room temperature for 2 h, so as to obtain a compound represented by Formula (m8) as a mixture (ESI-TOF MS m/z: 353.1575). After subjecting the reaction solution to vacuum concentration, the resulting residue was subjected to two azeotropic operations with dehydrated toluene. To the residue, 50 mL of dehydrated acetonitrile and 54 mL of a 28% aqueous ammonia solution (manufactured by Wako Pure Chemical Industries, Ltd.) were added, followed by stirring at room temperature for 1 h. After confirming elimination of the compound represented by Formula (m8) by ESI-TOF MS (m/z: 353.1575 changed to m/z: 300.1327), the resultant mixture was subjected to vacuum concentration with an evaporator. Ultrapure water was added to the residue, the resultant solution was washed with dichloromethane, and then the aqueous layer was concentrated with an evaporator and dried under reduced pressure. After the thus-obtained crude product was purified using alumina column chromatography (dichloromethane:methanol:water=12:6:1), methanol (manufactured by Nacalai Tesque) and amberlite (IRA96SB, manufactured by Organo Corporation) were added to the residue, and the resulting solution was stirred for 30 min. Thereafter, the amberlite was filtered out, and the resultant solution was concentrated and dried under reduced pressure, so as to obtain a $^{13}C/^{15}N$ labeled MPC represented by Formula (j1) (wherein a=2 and b=2) (a yellow viscous solid, 1.056 g, 3.52 mmol). The isolated yield was 90%.

Figure 2:
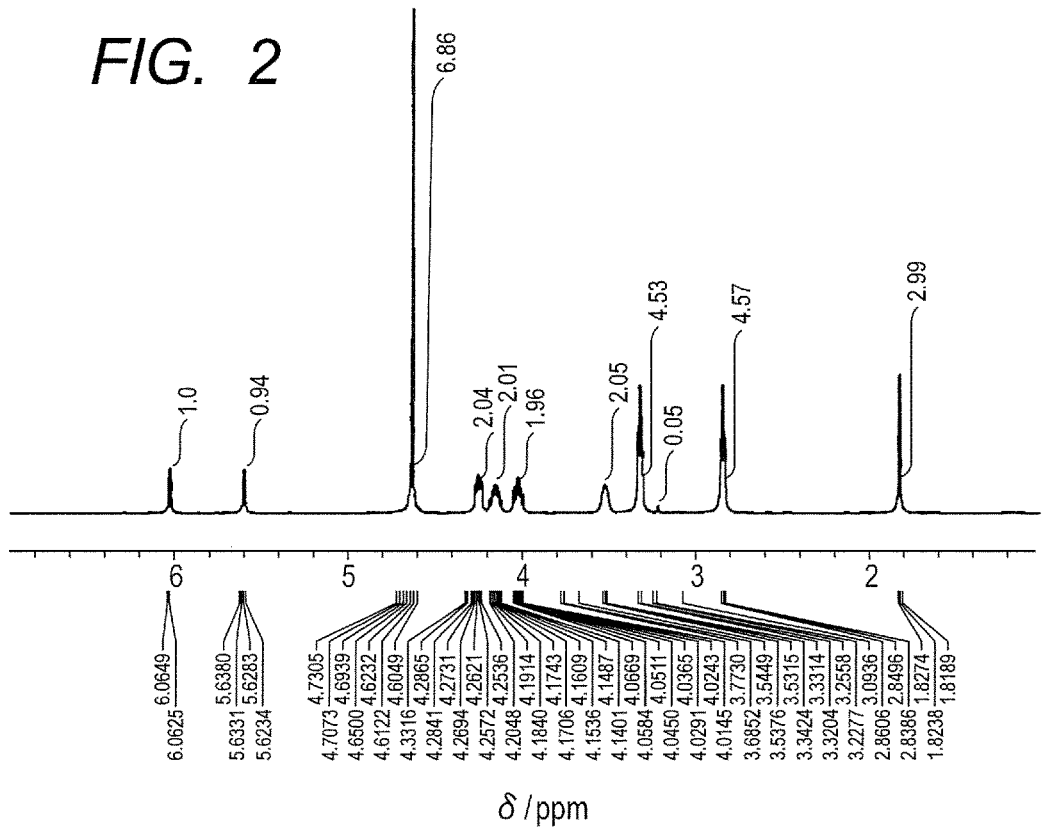
FIG. 2 is a $^1$H NMR spectrum of a $^{13}$C/$^{15}$N labeled MPC (of Formula (j1) wherein a=2 and b=2).

The $^1H$ NMR spectrum of Formula (j1) is illustrated in FIG. 2, and the spectrum data and the MS data thereof are as follows:

$^1H$ NMR spectrum (300 MHz, D$_2$O) δ/ppm=6.05-6.08 (1H, CH$_2$=C—), 5.52-5.66 (1H, CH$_2$=C—), 4.13-4.22 (2H, —OCH$_2$CH$_2$—OP—), 4.23-4.30 (2H, —OCH$_2$CH$_2$—OP—), 4.00-4.08 (2H, —OCH$_2$CH$_2$N), 3.50-3.58 (2H, —OCH$_2$CH$_2$N), 3.09 (dt, J=144.7, 3.30 Hz, 9H, $^{15}N(^{13}CH_3)_3$), 1.82 (t, J=1.28 Hz, 3H, —CH$_3$), ESI-TOF MS m/z: 300.1327 (M$^+$+H).

Figure 3:
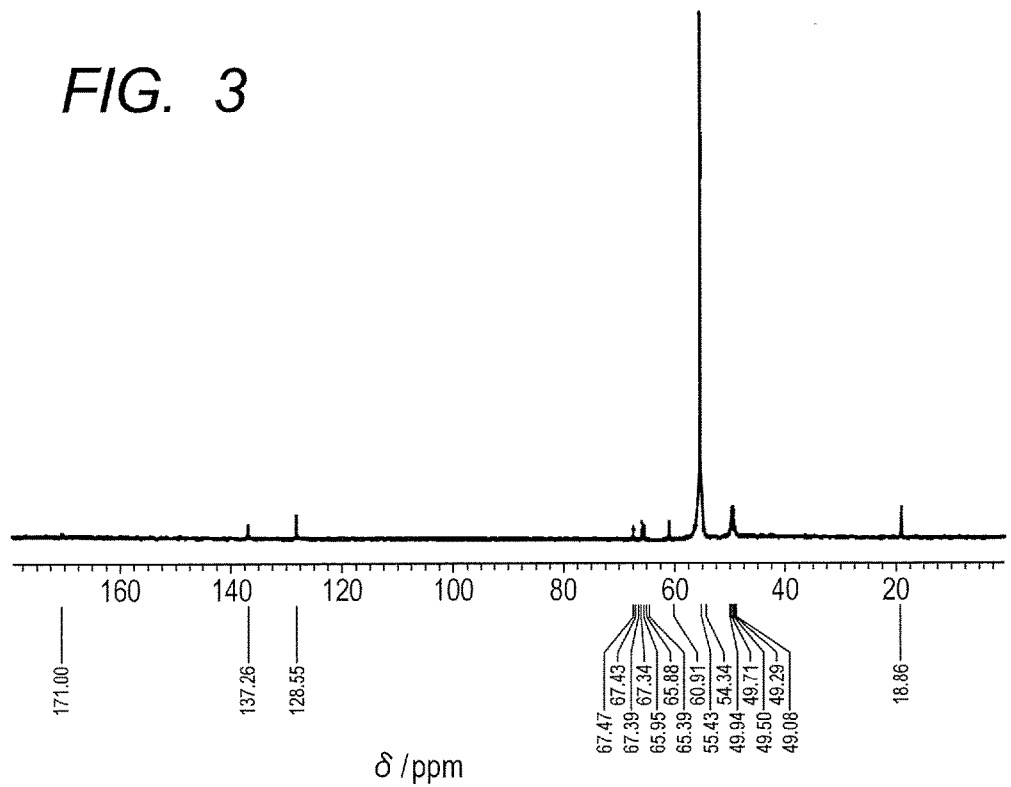
FIG. 3 is a $^{13}$C NMR spectrum of the $^{13}$C/$^{15}$N labeled MPC (of Formula (j1) wherein a=2 and b=2).

The $^{13}C$ NMR spectrum of Formula (j1) is illustrated in FIG. 3, and the spectrum data thereof are as follows:

$^{13}C$ NMR spectrum (100 MHz, D$_2$O/CD$_3$OD) δ/ppm=171.00, 137.26, 128.55, 67.41 (dd, $^2J_{CP}$=7.85, $^2J_{CN}$=4.55 Hz), 65.92 (d, $^2J_{CP}$=7.65 Hz), 65.39 (m), 60.91, 55.43 (d, $^1J_{CN}$=5.27 Hz), 18.86.

Figure 4:
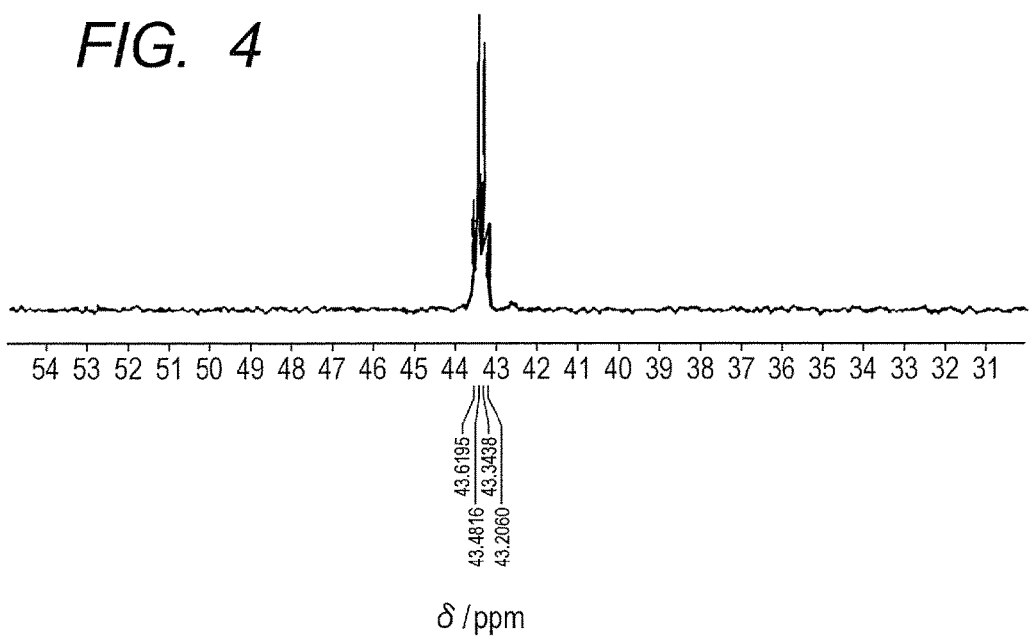
FIG. 4 is a $^{15}$N NMR spectrum of the $^{13}$C/$^{15}$N labeled MPC (of Formula (j1) wherein a=2 and b=2).

The $^{15}N$ NMR spectrum of Formula (j1) is illustrated in FIG. 4, and the spectrum data thereof are as follows:

$^{15}N$ NMR spectrum (40 MHz, D$_2$O/CD$_3$OD) δ/ppm=43.4 (q, $^1J_{CN}$=5.22 Hz).

Figure 5:
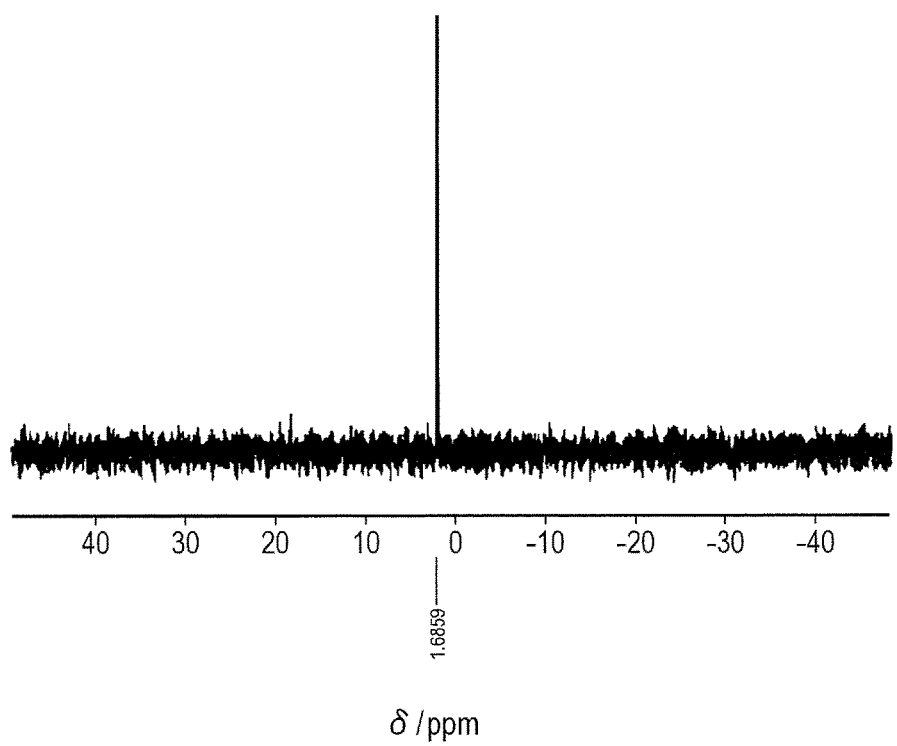
FIG. 5 is a $^{31}$P NMR spectrum of the $^{13}$C/$^{15}$N labeled MPC (of Formula (j1) wherein a=2 and b=2).

The $^{31}P$ NMR spectrum of Formula (j1) is illustrated in FIG. 5, and the spectrum data thereof are as follows:

$^{31}P$ NMR spectrum (160 MHz, D$_2$O) δ/ppm=1.69.

Example 2

Synthesis of $^{13}C/^{15}N$ Labeled PMPC (of Formula (p2)

A $^{13}C/^{15}N$ labeled PMPC represented by Formula (p2) was synthesized according to Reaction Formula 5:

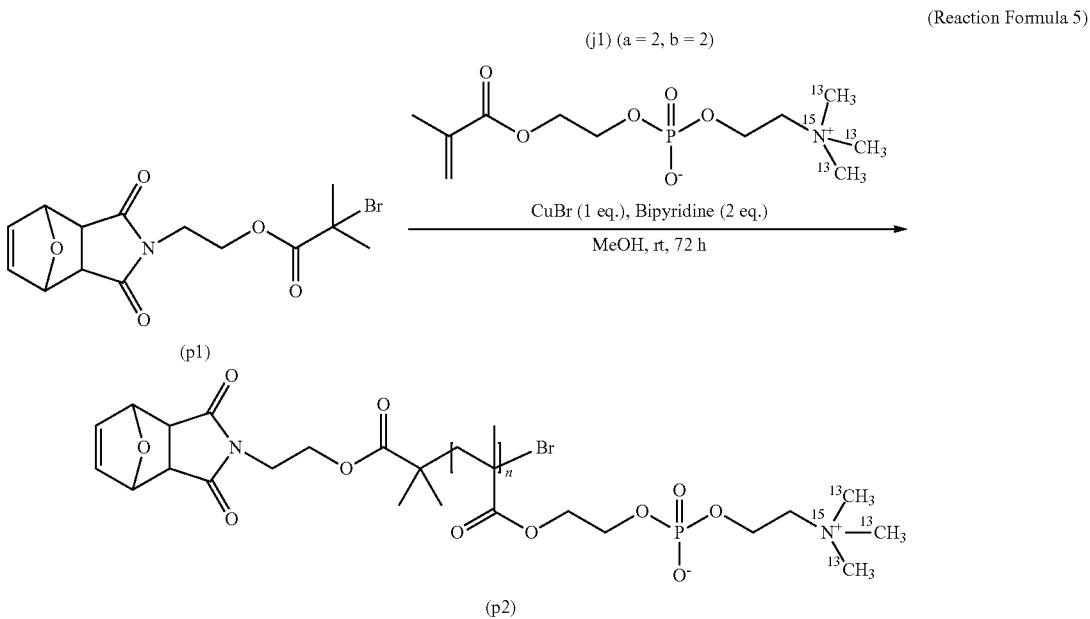

A 2 mL vial was charged with a $^{13}C/^{15}N$ labeled MPC represented by Formula (j1) (wherein a=2 and b=2) (135.6 mg, 0.46 mmol, 43 equiv, target number average molecular weight (M$_n$)=13000) and 0.3 mL of dehydrated methanol (manufactured by Nacalai Tesque), and Ar was allowed to flow through it for 30 min. Operations performed thereafter were conducted in a glove compartment under a nitrogen atmosphere. A polymerization initiator represented by Formula (p1) (3.5 mg, 0.01 mmol, 1 equiv) and 0.1 mL of a dehydrated methanol solution of CuBr (1.5 mg, 0.01 mmol, 1 equiv, manufactured by Wako Pure Chemical Industries, Ltd.) and 2,2'-bipyridine (3.1 mg, 0.02 mmol, 2 equiv, manufactured by Nacalai Tesque) were prepared. This solution was added to the reaction solution containing Formula (j1), and the resulting reaction solution was stirred at room temperature for 72 h. The solution became reddish brown. The end of the reaction was confirmed by $^1H$ NMR (monomer conversion of 98%). After stopping the reaction, the solution was passed through a thin silica gel layer to remove Cu (eluent: methanol), and the eluate was concentrated with an evaporator. Then, methanol and dehydrated THF were added to the residue, and the precipitate was collected, washed with dehydrated THF, and dried under reduced pressure. The crude product was purified by GPC (used column: SB-803HQ, eluent solvent: ultrapure water, flow rate: 1 mL/min, column temperature: 40° C.), and the purified product was lyophilized, so as to obtain a $^{13}$C/$^{15}$N labeled PMPC represented by Formula (p2) (white solid, Mn=6800). The isolated yield was 30%. The polymer represented by Formula (p2) prepared in this example is sometimes abbreviated as PMPC p2-1 (having n of Formula (p2) of 23, $M_n$ (GPC) of 6800 and $M_n$ (NMR) of 12000), PMPC p2-2 (having n of Formula (p2) of 16, $M_n$ (GPC) of 5000 and $M_n$ (NMR) of 10000), or PMPC p2-3 (having n of Formula (p2) of 40, $M_n$ (GPC) of 12000 and $M_n$ (NMR) of 18000).

Figure 6:
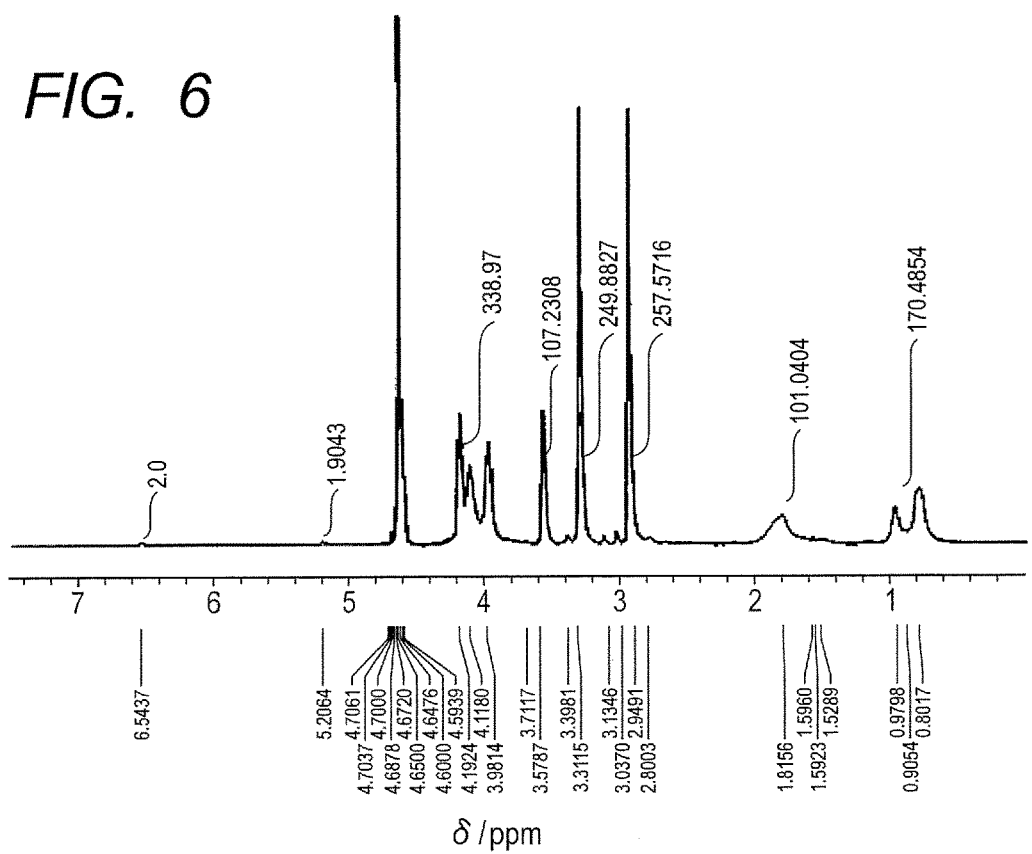
FIG. 6 is a $^1$H NMR spectrum of a $^{13}$C/$^{15}$N labeled PMPC p2-3 (of Formula (p2) wherein n=40, and $M_n$ (GPC)= 12000).

The $^1$H NMR spectrum of PMPC p2-3 is illustrated in FIG. 6, and the spectrum data thereof are as follows:

$^1$H NMR spectrum (400 MHz, D$_2$O) δ/ppm=6.54 (m, furan), 5.21 (m, furan), 4.15-4.31 (br, —OCH$_2$CH$_2$OP—, —NCH$_2$CH$_2$O—), 4.04-4.15 (br, —OCH$_2$CH$_2$OP—), 3.82-4.04 (br, POCH$_2$CH$_2^{15}$N—, —NCH$_2$CH$_2$O—), 3.51-3.62 (br, —CH$_2$N($^{13}$CH$_3$)$_3$), 3.14 (d, $^1J_{CH}$=144.8 Hz, —$^{15}$N($^{13}$CH$_3$)$_3$), 2.82-2.99 (—CHCON), 1.49-2.00 (br, —CH$_2$—, main chain, —C(CH$_3$)$_2$), 0.64-1.05 (br, —CH$_3$, main chain).

Figure 7:
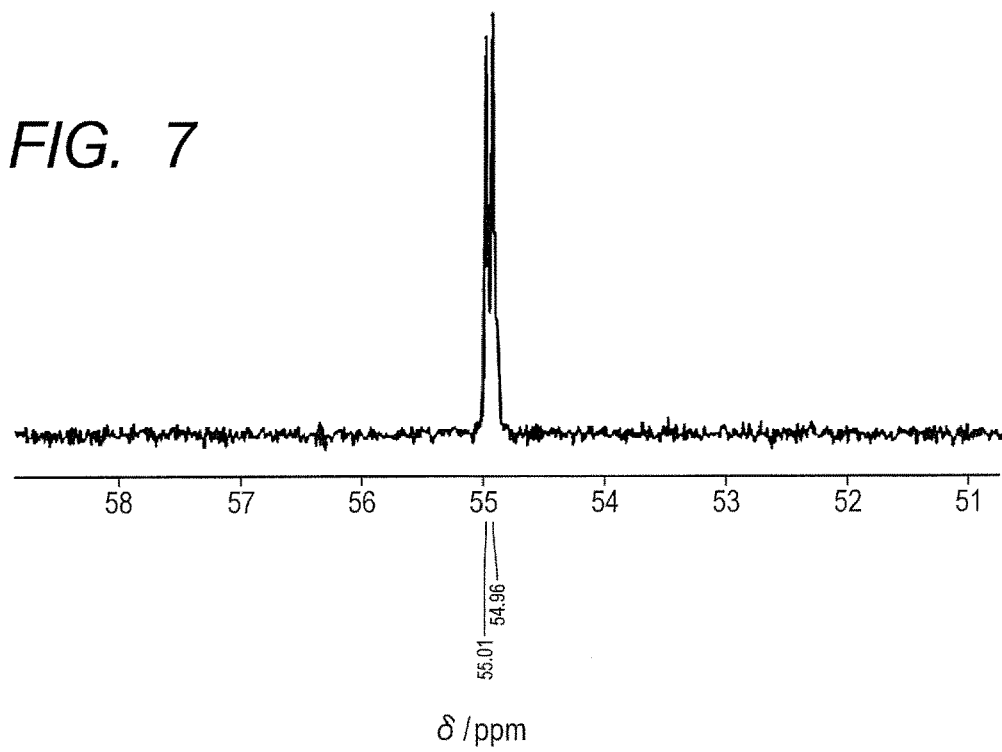
FIG. 7 is a $^{13}$C NMR spectrum of the $^{13}$C/$^{15}$N labeled PMPC p2-3 (of Formula (p2) wherein n=40, and $M_n$ (GPC)= 12000).

The $^{13}$C NMR spectrum of PMPC p2-3 is illustrated in FIG. 7, and the spectrum data thereof are as follows:

$^{13}$C NMR spectrum (100 MHz, D$_2$O/CD$_3$OD) labeled for $^{13}$C δ/ppm=55.0 (d, 1$J_{CN}$=5.02 Hz).

Figure 8:
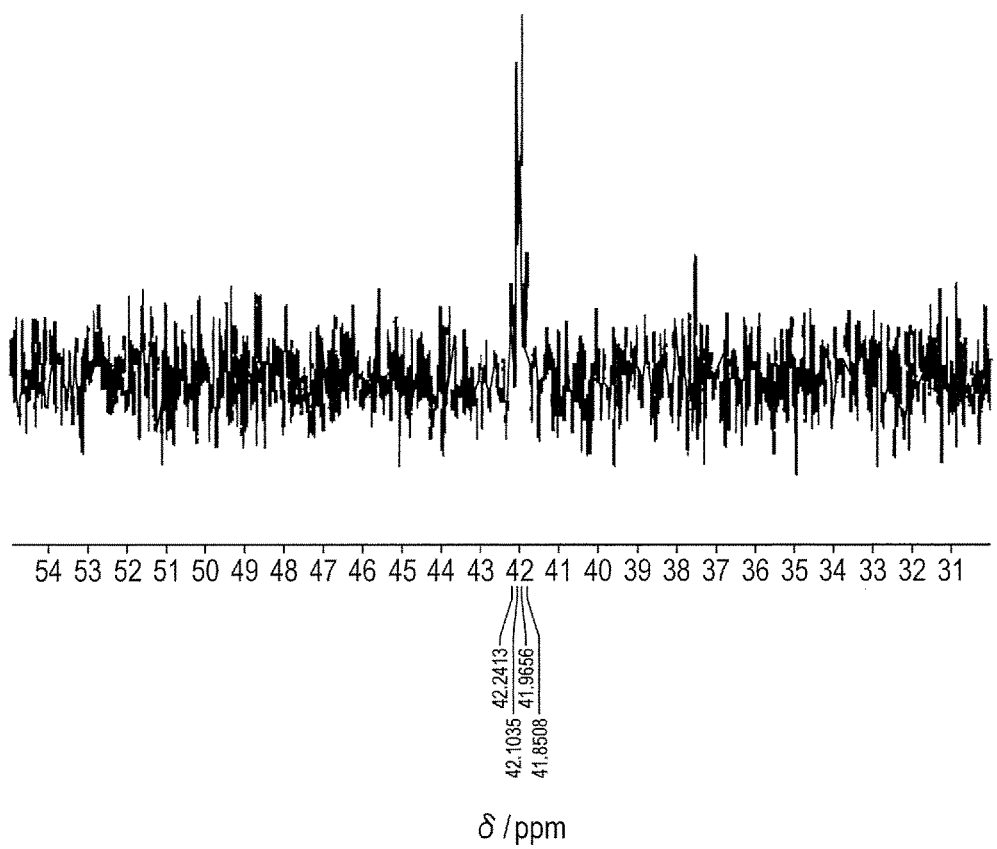
FIG. 8 is a $^{15}$N NMR spectrum of the $^{13}$C/$^{15}$N labeled PMPC p2-3 (of Formula (p2) wherein n=40, and $M_n$ (GPC)= 12000).

The $^{15}$N NMR spectrum of PMPC p2-3 is illustrated in FIG. 8, and the spectrum data thereof are as follows:

$^{15}$N NMR spectrum (40 MHz, D$_2$O/CD$_3$OD) labeled for $^{15}$N δ/ppm=42.0 (q, $J_{CN}$=5.21 Hz).

Figure 9:
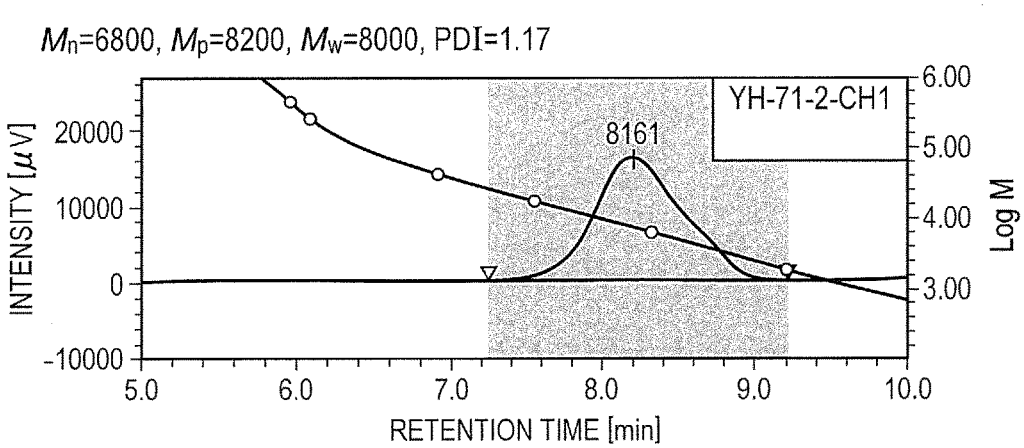
FIG. 9 is a GPC profile of a $^{13}$C/$^{15}$N labeled PMPC p2-1 (of Formula (p2) wherein n=23, and $M_n$ (GPC)=6800).

FIG. 9 illustrates a GPC profile of PMPC p2-1. The GPC measurement was conducted under the following conditions: used column: SB-803HQ, eluent solvent: 0.1 M NaNO$_3$ aq./0.2 wt % NaN$_3$, flow rate: 1 mL/min, and column temperature: 40° C. Each sample was filtered by a Millex-GV (0.22 μm) filter (Millipore Corporation) before injection.

Example 3

Figure 10:
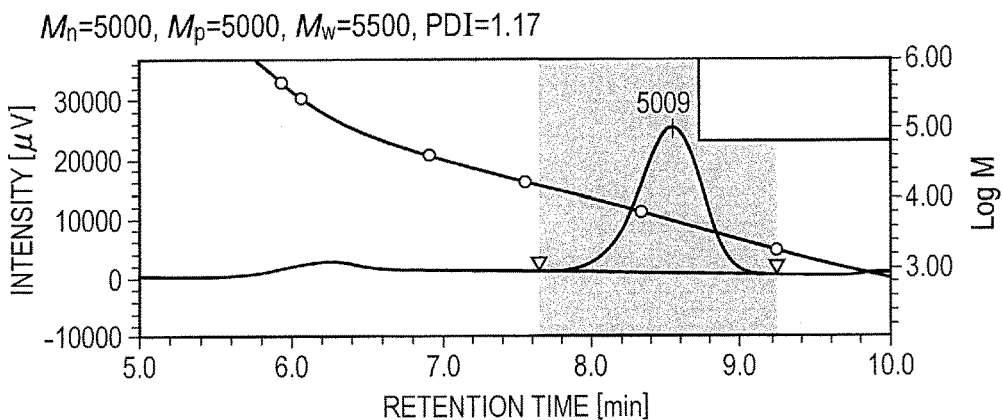
FIG. 10 is a GPC profile of a $^{13}$C/$^{15}$N labeled PMPC p2-2 (of Formula (p2) wherein n=16, and $M_n$ (GPC)=5000).
Figure 11:
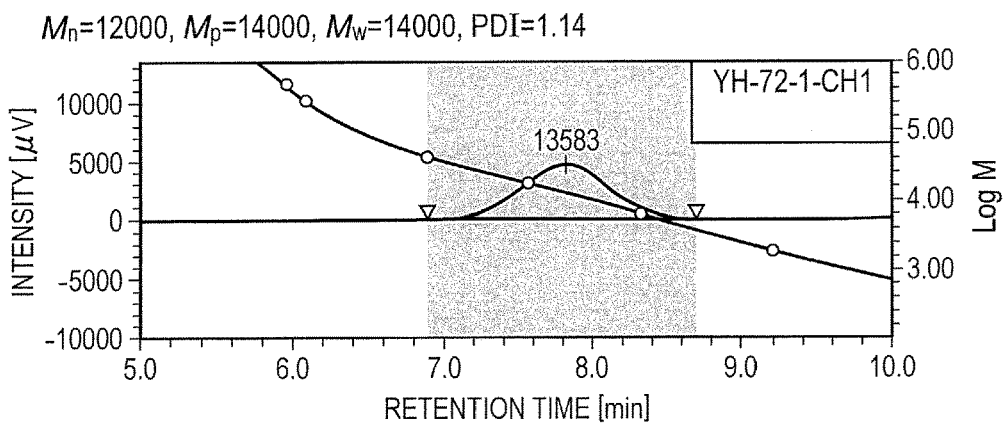
FIG. 11 is a GPC profile of a $^{13}$C/$^{15}$N labeled PMPC p2-3 (of Formula (p2) wherein n=40, and $M_n$ (GPC)=12000).

The equivalent amount of a monomer (of Formula (j1) (wherein a=2 and b=2)) to a synthesized polymerization initiator (of Formula (p1)) was changed in $^{13}$C/$^{15}$N labeled PMPC (PMPC p2-2 and PMPC p2-3) having different molecular weights, and an operation similar to that of Example 2 was performed, so as to obtain PMPC p2-2 having $M_n$ calculated based on the GPC of 5000 and a PMPC p2-3 having $M_n$ of 12000. The GPC charts of these PMPCs are illustrated in FIGS. 10 and 11, respectively. In addition, data of PMPC p2-1 to p2-3 are listed together in Table 1 below.

TABLE 1

| $^{13}$C/$^{15}$N labeled PMPC | Monomer unit | Target $M_n$ | Monomer conversion (%) | $M_n$ (NMR) | $M_n$ (GPC)[a] | PDI | Yield (%)[b] |
|---|---|---|---|---|---|---|---|
| PMPC p2-1 | 43 | 13000 | 98 | 12000 | 6800 | 1.17 | 30 |
| PMPC p2-2 | 35 | 10000 | 94 | 10000 | 5000 | 1.1 | 3 |
| PMPC p2-3 | 71 | 20000 | 94 | 18000 | 12000 | 1.14 | 13 |

[a] PEG standard
[b] Isolated yield based on GPC

In 72 h, a $^{13}$C/$^{15}$N labeled PMPC was obtained with monomer conversion of 94 to 98% with an isolated yield of 3 to 30%. As a result of GPC measurement of molecular weight calibrated with poly(ethylene glycol) (PEG), polydispersity index (PDI) was found to have a value of 1.10 to 1.17, which shows that the synthesized $^{13}$C/$^{15}$N labeled PMPC polymer was quite close to being monodisperse.

Furthermore, when no polymerization initiator was added to the reaction solution as a reference experiment, the polymerization reaction did not proceed at all, and the targeted polymer could not be obtained (as confirmed by $^1$H NMR and GPC). This result suggests that spontaneous polymerization of the $^{13}$C/$^{15}$N labeled MPC did not occur but a living radical polymerization reaction had proceeded from the polymerization initiator.

Example 4

Setting of INEPT-Based Pulse Sequence for Triple Resonance NMR

Figure 12:
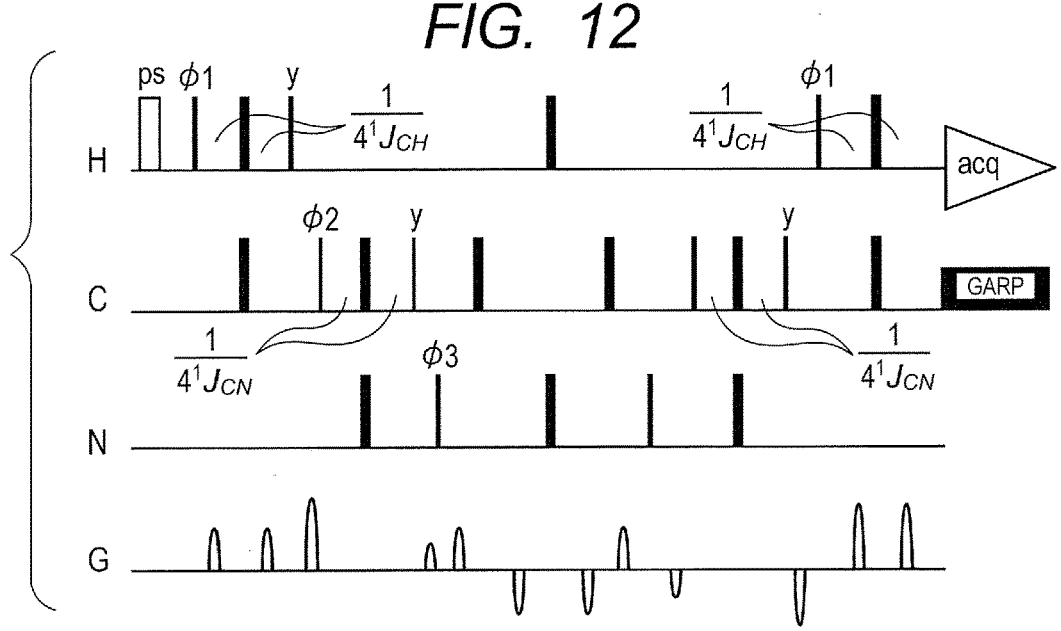
FIG. 12 is a pulse sequence for $^1$H—{$^{13}$C—$^{15}$N} triple resonance NMR.

An INEPT-based pulse sequence for triple resonance illustrated in FIG. 12 was used. In FIG. 12, the narrow and broad filled bars represent 90° pulses and 180° pulses, respectively.

Based on the $^1$H NMR of the $^{13}$C/$^{15}$N labeled PMPC p2-3, peaks attributed to $^1$H derived from a furan ring of the polymerization initiator were observed at 6.54 ppm and 5.21 ppm. In addition, a doublet peak of a methyl group coupled with $^{13}$C was observed, and a coupling constant ($^1J_{CH}$) of $^1$H—$^{13}$C was calculated as $^1J_{CH}$=144.8 Hz (FIG. 6). Furthermore, a peak of a methyl group at 55.0 ppm was confirmed in the $^{13}$C NMR, a peak of quaternary ammonium at 42.0 ppm was confirmed in the $^{15}$N NMR, and a coupling constant ($^1J_{CN}$) of $^{13}$C—$^{15}$N was calculated as $^1J_{CN}$=5.21 Hz (FIGS. 7 and 8). Based on these data, a $^1$H—{$^{13}$C—$^{15}$N} triple resonance signal of the PMPC p2-1 can be selectively observed by setting offsets (chemical shifts) of $^{13}$C and $^{15}$N respectively to $^{13}$C=55.0 ppm and $^{15}$N=42.0 ppm and setting delay intervals (coupling constants) of FIG. 12 to ¼$^1J_{CH}$=1.73 ms and ¼$^1J_{CN}$=48 ms.

Example 5

$^1$H—{$^{13}$C—$^{15}$N} Triple Resonance NMR of $^{13}$C/$^{15}$N Labeled PMPC p2-3 in a Complex System The NMR spectrum of PMPC p2-3 was measured in a mouse liver extract including a large number of proteins and amino acids, so as to examine the influence of the molecular weight increase on the selectivity for a $^1$H-{$^{13}$C—$^{15}$N} triple resonance NMR signal.

First, mouse liver tissues were harvested and homogenized. The homogenate and the PMPC p2-3 in 1 μM (a molar concentration calculated using $M_n$ (GPC)) were mixed and lyophilized to dryness, dissolved in a $D_2O$ solution, and subjected to NMR analysis.

In the general $^1H$ NMR, a large number of $^1H$ signals were observed, and hence it was impossible to detect a $^1H$ signal derived from a methyl group of the PMPC p2-3 (FIG. 13A).

In contrast, in a $^1H$—{$^{13}C$} double resonance NMR spectrum of the same sample, although the selectivity was improved as compared with that in the $^1H$ NMR, $^1H$ signals derived from contaminations included in the liver extract were so strongly observed that it was impossible to detect highly selectively a $^1H$ signal derived from a methyl group of PMPC p2-3 (FIG. 13B). When the measurement was further performed using the $^1H$—{$^{13}C$—$^{15}N$} triple resonance NMR, only a $^1H$ signal at 3.14 ppm derived from a methyl group of the PMPC p2-3 was observed (FIG. 13C).

It was shown, based on the aforementioned results, that a $^1H$ signal derived from a methyl group of PMPC p2-3 can be highly selectively detected even in an organism system containing a large number of contaminations by employing $^1H$—{$^{13}C$—$^{15}N$} triple resonance NMR.

In the $^1H$—{C—$^{15}N$} triple resonance NMR spectrum, a noise peak was observed at 3.67 ppm (FIG. 13C). For this peak, there is a possibility that noise derived from magnetization remaining in a sequence, other than the $^1H$—$^{13}C$—$^{15}N$ sequence, included in the contaminations is observed. However, it is considered that this noise intensity may be lowered by optimizing a parameter of the phase cycling or the like of the pulse sequence. With respect to the $^{13}C/^{15}N$ labeled PMPC p2-3 (1 μM (a molar concentration calculated using $M_n$ (GPC)) in a 10 mM tris-HCl buffer (pH 8.0) including a mouse liver extract (10% v/v) and 2-mercaptoethanol (0.5 mM), the $^1H$ NMR (FIG. 13A), the $^1H$—{$^{13}C$} double resonance NMR (FIG. 13B) and the $^1H$—{$^{13}C$—$^{15}N$} triple resonance NMR (number of scans: 256) (FIG. 13C) are shown.

Example 6

Macromolecular Effect (Effect of Accumulation of Stable Isotopes) on Signal Sensitivity Next, the macromolecular effect on the signal sensitivity was examined. Considering application to MR imaging, three types of $^{13}C/^{15}N$ labeled PMPC (p2-1 to p2-3) having $M_n$ (GPC) of 5000 (16 units), 6800 (23 units) and 12000 (40 units) were evaluated in $D_2O$ with a measuring time of 8 min (number of scans: 256) by using the $^1H$—{$^{13}C$—$^{15}N$} triple resonance NMR (FIG. 14A). In all of the $^{13}C/^{15}N$ labeled PMPC having any molecular weight, a signal-noise ratio (S/N) was linearly decreased along with a decrease in the polymer concentration. Furthermore, when the concentrations were the same, the S/N was increased in proportion to the number of monomer units. The $^{13}C/^{15}N$ labeled MPC (of Formula (j1)) (wherein a=2 and b=2) of 1 μM had a S/N of 8.72, but the $^{13}C/^{15}N$ labeled PMPC p2-3 of 1 μM (a molar concentration calculated by $M_n$ (GPC)) having stable isotopes accumulated by increasing the molecular weight attained S/N of 221, and thus, the signal intensity was increased by approximately 25 times. Furthermore, the detection limit of the $^{13}C/^{15}N$ labeled PMPC p2-3 was checked, and the $^{13}C/^{15}N$ labeled PMPC even at 50 nM (corresponding to 30 nM calculated as a molar concentration by $M_n$ (NMR)) had a S/N of 17.5, and a clear signal was observed (FIG. 14B).

It was shown, based on these results, that the signal intensity can be remarkably increased so as to be detectable with high sensitivity of the order of nM in $^{13}C/^{15}N$ labeled PMPC in which stable isotopes are accumulated by increasing the molecular weight.

A graph illustrating the relationship between the concentration (molar concentration calculated using the $M_n$ (GPC)) and the S/N of the $^{13}C/^{15}N$ labeled MPC and the $^{13}C/^{15}N$ labeled PMPC p2-1 to p2-3 obtained by the $^1H$—{$^{13}C$—$^{15}N$} triple resonance NMR performed in $D_2O$ is given in FIG. 14A, and $^1H$—{$^{13}C$—$^{15}N$} triple resonance NMR spectra (number of scans: 256) in $D_2O$ obtained at various concentrations (from 50 nM to 1 μM: a molar concentration calculated by $M_n$ (GPC)) of the $^{13}C/^{15}N$ labeled PMPC p2-3 are given in FIG. 14B.

Example 7

Preparation of Single Chain Antibody hu4D5-8scFv

Based on a gene sequence (hu4D5-8) of a variable region of IgG bound to Her2, a gene hu4D5-8scFv encoding a single chain antibody (scFv) was produced. First, VL and VH genes of the hu4D5-8 were linked by a cDNA encoding peptide (GGGGS) 3 so as to produce a cDNA. A restriction enzyme NcoI- was introduced into the 5'-end, and a recognition site for a restriction enzyme NotI was introduced into the 3'-end. The nucleotide sequence is as follows:

(Seq. ID Number 1)

5'-
<u>CCATG</u>GATATCCAGATGACCCAGTCCCCGAGCTCCCTGTCCGCCTCTGTG

GGCGATAGGGTCACCATCACCTGCCGTGCCAGTCAGGATGTGAATACTGC

TGTAGCCTGGTATCAACAGAAACCAGGAAAAGCTCCGAAACTACTGATTT

ACTCGGCATCCTTCCTCTACTCTGGAGTCCCTTCTCGCTTCTCTGGATCC

AGATCTGGGACGGATTTCACTCTGACCATCAGCAGTCTGCAGCCGGAAGA

CTTCGCAACTTATTACTGTCAGCAACATTATACTACTCCTCCCACGTTCG

GACAGGGTACCAAGGTGGAGATCAAAGGCGGTGGTGGCAGCGGTGGCGGT

GGCAGCGGCGGTGGCGGTAGCGAGGTTCAGCTGGTGGAGTCTGGCGGTGG

CCTGGTGCAGCCAGGGGGCTCACTCCGTTTGTCCTGTGCAGCTTCTGGCT

TCAACATTAAAGACACCTATATACACTGGGTGCGTCAGGCCCCGGGTAAG

GGCCTGGAATGGGTTGCAAGGATTTATCCTACGAATGGTTATACTAGATA

TGCCGATAGCGTCAAGGGCCGTTTCACTATAAGCGCAGACACATCCAAAA

ACACAGCCTACCTGCAGATGAACAGCCTGCGTGCTGAGGACACTGCCGTC

TATTATTGTTCTAGATGGGAGGGGACGGCTTCTATGCTATGGACTACTG

GGGTCAAGGAACCCTGGTCACCGTCTCCTCG<u>GCGGCCGC</u>-3'

(The recognition sites for the restriction enzymes are underlined.)

This gene fragment hu4D5-8scFv was inserted downstream of the T7/lac promoter of plasmid pET-22b (+) (manufactured by Novagen, Inc.). Specifically, the cDNA obtained above was ligated to pET-22b (+) having been subjected to a digestion treatment with the restriction enzymes NcoI- and NotI.

The resulting expression plasmid was transformed into Escherichia coli BL21 (DE3) so as to obtain a strain for expression. The thus obtained strain was cultured in 4 mL of an LB-Amp medium overnight, and the whole volume was added to 250 mL of a 2×YT medium, followed by shaking the culture at 28° C. and 120 rpm for 8 hours. Thereafter, IPTG (isopropyl-β-D (−)-thiogalactopyranoside) was added thereto to attain a final concentration of 1 mM, and the resultant mixture was cultured overnight at 28° C. The cultured *Escherichia coli* were subjected to centrifugal separation at 8000×g and 4° C. for 30 min, and the supernatant culture broth was collected. Ammonium sulfate in an amount corresponding to 60 wt % of the culture broth was added to the thus-obtained culture broth to precipitate the protein by salting out. The solution having been subjected to the salting out was allowed to stand at 4° C. overnight and then subjected to centrifugal separation at 8000×g and 4° C. for 30 min so as to collect the precipitate. The obtained precipitate was dissolved in a 20 mM tris HCl/500 mM NaCl buffer and dialyzed with 1 L of this buffer. The dialyzed protein solution was added to a column filled with His Bind (registered trademark) Resin (manufactured by Novagen, Inc.) and purified by metal chelate affinity chromatography using Ni ions. The thus purified hu4D5-8scFv was confirmed, by reduction SDS-PAGE, to appear as a single band and to have a molecular weight of approximately 27 kDa. The amino acid sequence of the prepared antibody is as follows. Hereinafter, hu4D5-8scFv is abbreviated as scFv.

(Seq. ID Number 2)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASGFN

IKDTYIHWVRQAPGKGLEWVARIYPTNGYTRYADSVKGRFTISADTSKNT

AYLQMNSLRAEDTAVYYCSRWGGDGFYAMDYWGQGTLVTVSSAAALEHHH

HHHGGC

Example 8

Figure 16:
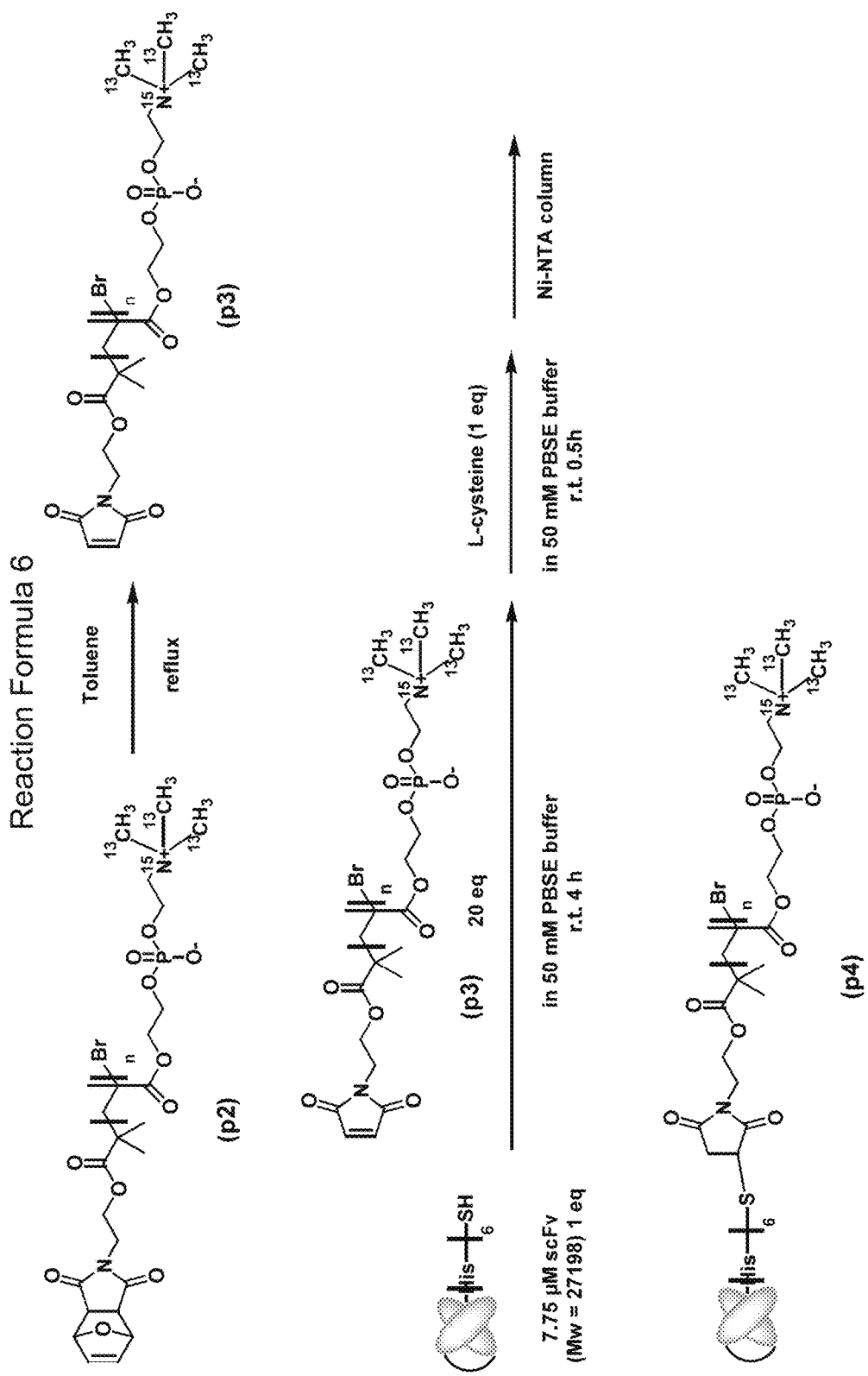
FIG. 16 shows Reaction Formula 6.

The $^{13}C/^{15}N$ labeled PMPC p2-1 (of Formula (p2)) was used as a polymer tag that transmits a multiple resonance signal so as to tag scFv that was an artificial antibody having a region for recognizing a Her2 antigen of breast cancer (Reaction Formula 6, shown in FIG. 16).

(Retro-Diels-Alder Reaction of Protecting Group at an End of the Polymer)

A glass reaction tube was charged with the $^{13}C/^{15}N$ labeled PMPC p2-1 ($M_n$ (GPC)=6800, $M_n$ (NMR)=12000) (34.8 mg, 4.99 mmol) obtained in Example 2 and 1 mL of dehydrated toluene (manufactured by Wako Pure Chemical Industries, Ltd.), followed by heating at reflux under an Ar atmosphere for 48 h. After stopping the reaction, the resultant solution was concentrated with an evaporator and dried under reduced pressure. To the residue, methanol and dehydrated THF were added, and a precipitate was collected to obtain a PMPC p3 (yellow solid) represented by Formula (p3). The $^1H$ NMR measurement was conducted on the obtained polymer, resulting in the finding that a peak derived from a furan ring had been eliminated, and a signal derived from a maleimide group was observed at 6.85 ppm.

(Immobilization of scFv onto $^{13}C/^{15}N$ Labeled PMPC)

Next, a 1.5 mL Snap Lock Micro-tube was charged with 100 μL of 7.75 μM scFv (5 mM PBS-EDTA buffer) and 1.5 μL of 10 mM tris(2-carboxyethyl)phosphine hydrochloride (TCEP-HCl) (5 mM PBS-EDTA buffer), and the resulting solution was slowly mixed at room temperature for 2 h. Subsequently, 1.47 μL of an aqueous solution of the PMPC p3 (10 mM) filtered by a Millex-LH (0.45 μm) filter (Millipore Corporation) was added thereto, and the resulting solution was slowly mixed at room temperature for 4 h. Thereafter, 1.5 μL of 10 mM L-cysteine (manufactured by Nacalai Tesque) (5 mM PBS-EDTA buffer) was added thereto, and the resulting solution was slowly mixed at room temperature for 30 min.

The reaction solution was transferred to an Amicon Ultra filtration tube (molecular weight cutoff 10 KDa) and concentrated by centrifuging (14000×g) for 20 minutes. To the concentrated solution, 100 μL of a binding buffer (1× phosphate, 20 mM imidazole) was added, and the resultant was centrifuged (14000×g) for 10 min. This operation was repeated twice with substitution of the buffer. The mixture was purified using a Ni affinity column (His Spin Trap (trademark), GE Healthcare) and concentrated using an Amicon Ultra filtration tube (molecular weight cut off 10 KDa), and to the resultant solution, 400 μL of 5 mM PBS-EDTA was added, followed by centrifuging (14000×g) for 30 min. This operation was repeated twice, so as to obtain a mixture of PMPC p4 (of Formula (p4))-scFv conjugate and unreacted scFv. Incidentally, production of the PMPC p4-scFv conjugate was confirmed using an SDS-PAGE (4-20%) measurement.

Example 9

Figures 15A, 15B, 15C:
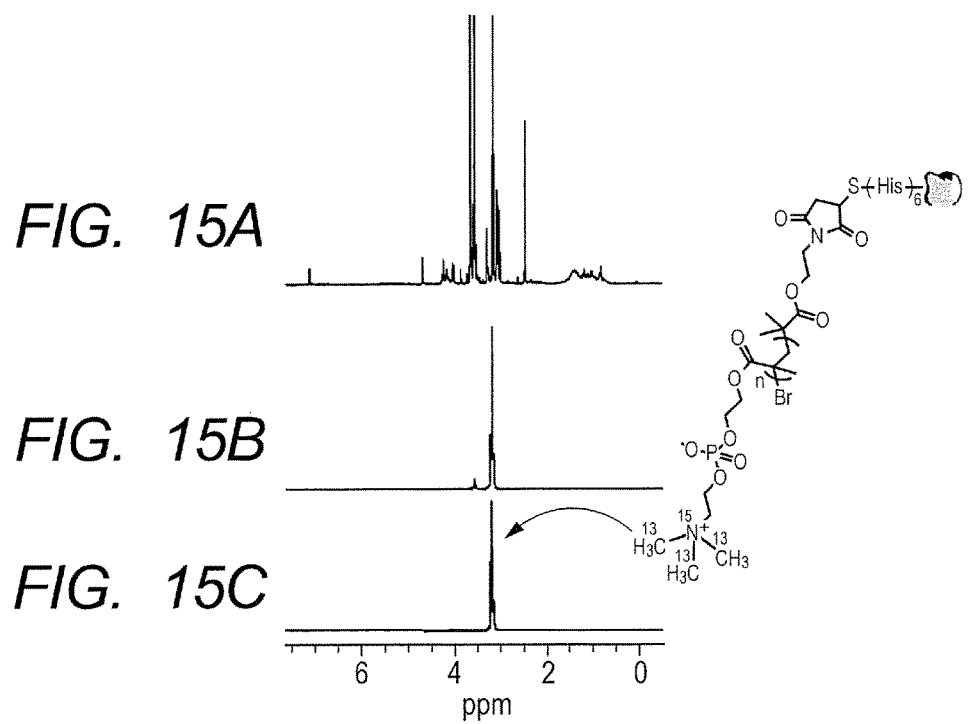
FIG. 15A is a $^1$H NMR spectrum of a $^{13}$C/$^{15}$N labeled PMPC p4-scFv conjugate.
FIG. 15B is a $^1$H—{$^{13}$C} double resonance NMR spectrum of the $^{13}$C/$^{15}$N labeled PMPC p4-scFv conjugate.
FIG. 15C is a $^1$H—{$^{13}$C—$^{15}$N} triple resonance NMR spectrum of the $^{13}$C/$^{15}$N labeled PMPC p4-scFv conjugate.

$^1H$—$\{^{13}C$—$^{15}N\}$ Triple Resonance NMR of $^{13}C/^{15}N$ Labeled PMPC p4 Having scFv Immobilized Thereon The NMR spectrum of the $^{13}C/^{15}N$ labeled PMPC p4 (of Formula (p4))-scFv conjugate was measured. In the general $^1H$ NMR, a $^1H$ signal derived from a methyl group of the $^{13}C/^{15}N$ labeled PMPC as well as all $^1H$ signals derived from scFv and the buffers were observed (FIG. 15A). In the $^1H$—$\{^{13}C\}$ double resonance NMR, a $^1H$ signal derived from a methyl group of the $^{13}C/^{15}N$ labeled PMPC-scFv conjugate was more clearly detected at 3.14 ppm, but a $^1H$ signal derived from scFv or the buffer was also observed at 3.55 ppm (FIG. 15B).

In contrast, when the $^1H$—$\{^{3}C$—$^{15}N\}$ triple resonance NMR was measured, only a $^1H$ signal derived from a methyl group of the $^{13}C/^{15}N$ labeled PMPC-scFv conjugate was observed (FIG. 15C). It was confirmed, based on these results, that an anti-Her2 artificial antibody scFv can be tagged with a $^{13}C/^{15}N$ labeled PMPC and can be highly selectively detected by $^1H$—$\{^{13}C$—$^{15}N\}$ triple resonance NMR. Consequently, it was shown that a polymer having, in its side chains, the $^1H$—$^{13}C$—$^{15}N$ sequence represented by Formula (y1) can be highly selectively detected, and according to a similar principle, the $^1H$—$^{13}C$—$^{13}C$ sequence represented by Formula (y2) and the $^1H$—$^{15}N$—$^{13}C$ sequence represented by Formula (y3) can be similarly highly selectively detected.

With respect to the $^{13}C/^{15}N$ labeled PMPC p4-scFv conjugate, the $^1H$ NMR (FIG. 15A), the $^1H$—$\{^{13}C\}$ double resonance NMR (FIG. 15B) and the $^1H$—$\{^{13}C$—$^{15}N\}$ triple resonance NMR (700 MHz, in $D_2O$) (FIG. 15C) are shown.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-118061, filed May 23, 2012, which is hereby incorporated by reference herein in its entirety.

The invention claimed is:

1. A straight-chain polymer having a main chain consisting of a repeating unit of formula (x1) and terminal end groups at ends thereof, the polymer having a degree of polymerization of 10 to 1000:

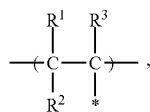
(x1)

wherein a side chain of each of the repeating units is a structure of formula (y1):

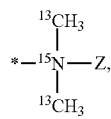
(y1)

wherein:
in the formula (x1), each of $R^1$ to $R^3$ independently represents a hydrogen atom, or a substituted or unsubstituted hydrocarbon group having one to four carbon atoms,
in the formula (x1), * (an asterisk) represents a bond to the formula (y1) directly or via a linker,
in the formula (y1), * (an asterisk) represents a bond to the formula (x1) directly or via a linker,
in the formula (y1), Z represents a monovalent atom or a monovalent atom group, and
a substituent of each of $R^1$ to $R^3$ is a functional group including at least one selected from the group consisting of a halogen atom, an oxygen atom, and a nitrogen atom.

2. The polymer according to claim 1, wherein the linker and the side chain are selected from the group consisting of formulas (y5) to (y7):

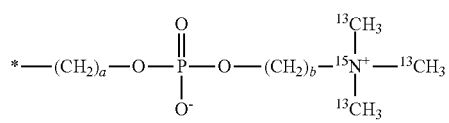
(y5)

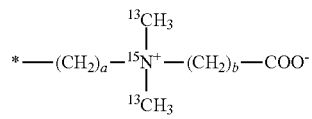
(y6)

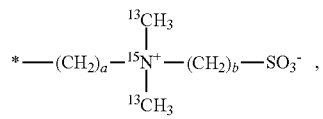
(y7)

wherein:
in the formulas (y5) to (y7), * (an asterisk) represents a bond to the formula (x1), and
each of a and b independently represents an integer of one to four, and a hydrogen atom of a methylene group in the formulas (y5) to (y7) is optionally replaced by another atom.

3. The polymer according to claim 1, wherein the repeating unit is represented by formula (I):

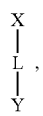
(I)

wherein:
in the formula (I), X represents the formula (x1),
L represents a direct bond, or a divalent atom or a divalent atom group,
if L is the divalent atom or the divalent atom group, L binds to X or Y of the formula (I),
Y represents the formula (y1),
in the formula (x1), * (an asterisk) represents a bond to L of the formula (I), or a bond to Y if L is a direct bond, and
in the formula (y1), * (an asterisk) represents a bond to L of the formula (I), or a bond to X if L is a direct bond.

4. The polymer according to claim 3, wherein L of the formula (I) is selected from the group consisting of a substituted or unsubstituted hydrocarbon group having one to four carbon atoms and formulas (l1) to (l3):

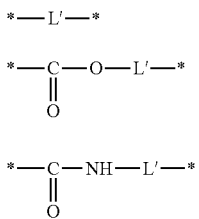  (11)

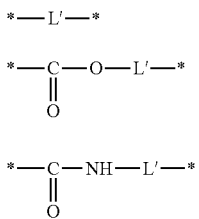  (12)

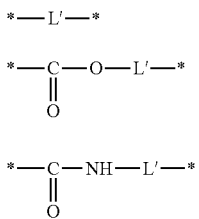  (13)

wherein:

in the formulas (l1) to (l3), * (an asterisk) represents a bond to X or Y of the formula (I), a substituent of the hydrocarbon group is a functional group including at least one selected from the group consisting of a halogen atom, an oxygen atom, and a nitrogen atom, and L' of the formulas (l1) to (l3) is selected from the group consisting of a substituted or unsubstituted hydrocarbon group having one to four carbon atoms and formula (l'):

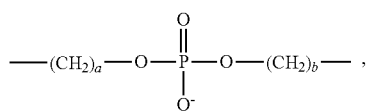  (l')

wherein:

in the formula (l'), each of a and b independently represents an integer of one to four, and the hydrocarbon group having one to four carbon atoms of L' and a hydrogen atom of a methylene group of the formula (l') are optionally replaced by another atom.

5. The polymer according to claim 1, wherein Z of the formula (y1) is represented by formula (z1) or (z2):

*—$^{15}NH_2$  (z1)

*—$^{13}CH_3$  (z2), wherein:

in the formulas (z1) and (z2), * (an asterisk) represents a bond to $^{15}N$ of the formula (y1).

6. The polymer according to claim 1, wherein Z of the formula (y1) is represented by formula (z3) or (z4):

*—$(CH_2)_d$—COO$^-$  (z3)

*—$(CH_2)_d$—SO$_3^-$  (z4)

wherein:

in the formulas (z3) and (z4), * (an asterisk) represents a bond to $^{15}N$ of the formula (y1), and in the formulas (z3) and (z4), d represents an integer of one to four, and a hydrogen atom of a methylene group is optionally replaced by another atom.

7. The polymer according to claim 1, represented by any one of formulas (i1) to (i12):

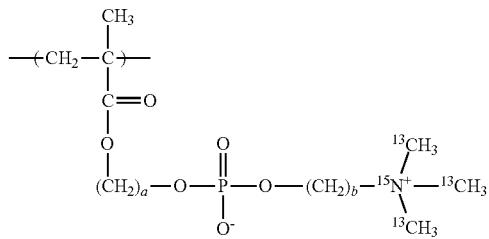  (i1)

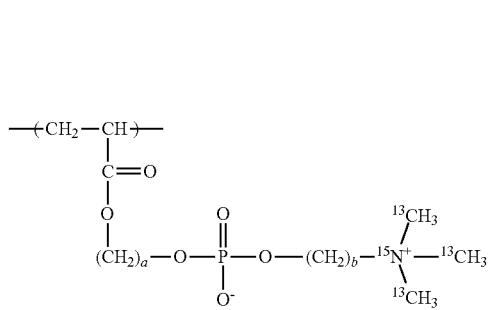  (i2)

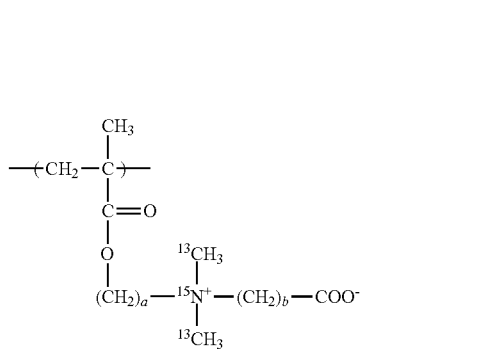  (i3)

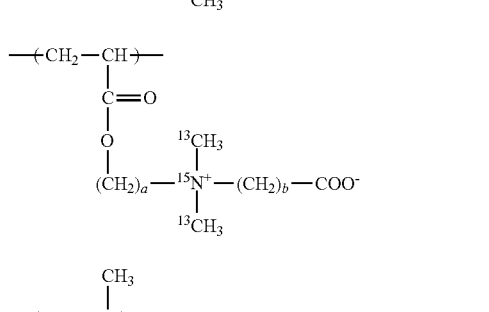  (i4)

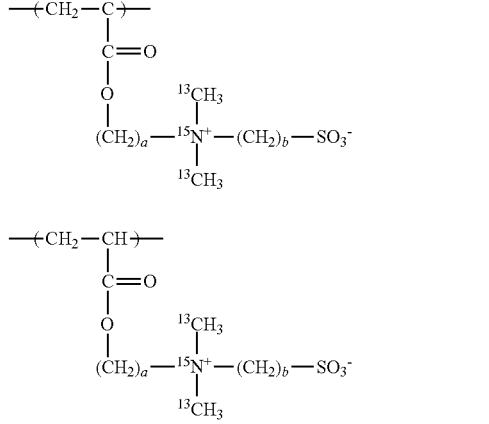  (i5)

(i6)

-continued

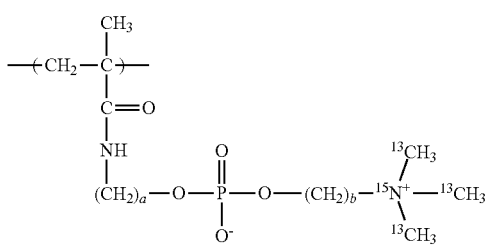
(i7)

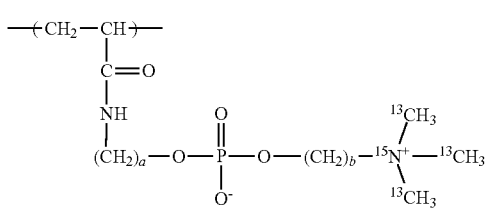
(i8)

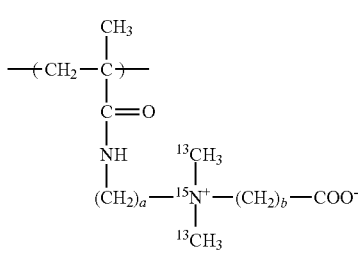
(i9)

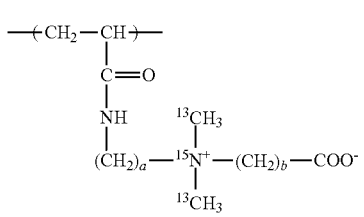
(i10)

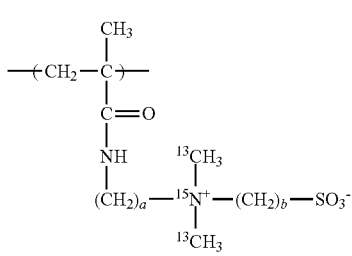
(i11)

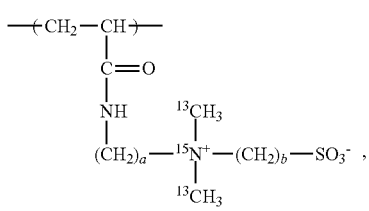
(i12)

wherein, in the formulas (i1) to (i12), each of a and b independently represents an integer of one to four, and a hydrogen atom of a methylene group is optionally replaced by another atom.

8. The polymer according to claim 1, wherein the polymer has the degree of polymerization of 10 to 400.

9. The polymer according to claim 1, wherein the polymer has, at an end of the main chain, any one of an N-hydroxysuccinimide group, a maleimide group, an amino group, an azide group, an ethynyl group, a vinyl group, a trichlorosilyl group, a thiol group, a hydroxyl group, and an alkyl group.

10. A compound comprising the polymer according to claim 1 and a trapping molecule that specifically binds to a target site.

11. The polymer according to claim 1, comprising two or more different side chains.

12. The polymer according to claim 1, wherein the side chain of the each repeating unit is the same.

13. The polymer according to claim 1, the one repeating unit is selected from the group consisting of a repeating unit derived from a methacrylate monomer, a repeating unit derived from a methacrylamide monomer, a repeating unit derived from an amino acid monomer, and a repeating unit derived from a hydroxy acid monomer.

14. A contrast agent for nuclear magnetic resonance analysis or magnetic resonance imaging, comprising the polymer according to claim 1 and a dispersion medium.

15. A compound represented by any one of formulas (j1) to (j12):

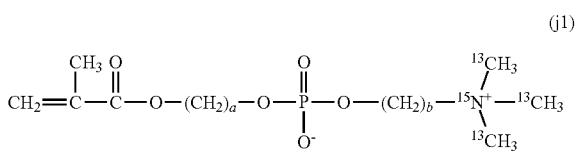
(j1)

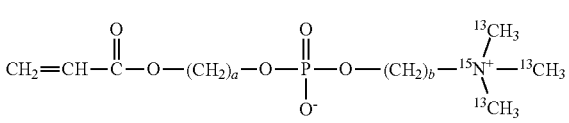
(j2)

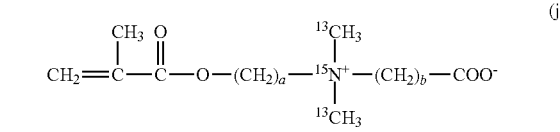
(j3)

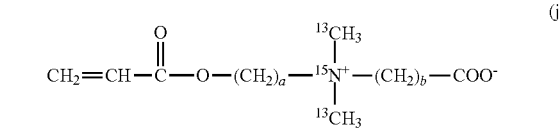
(j4)

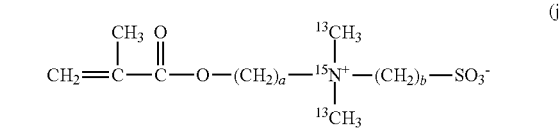
(j5)

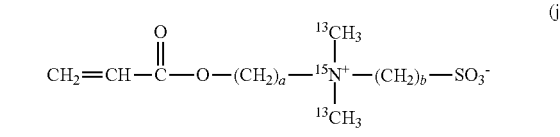
(j6)

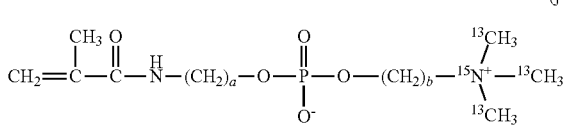
(j7)

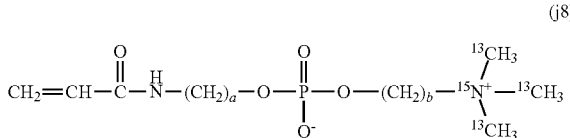
(j8)

-continued

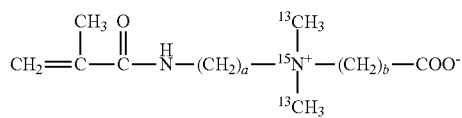
(j9)

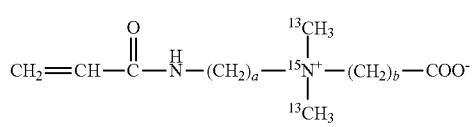
(j10)

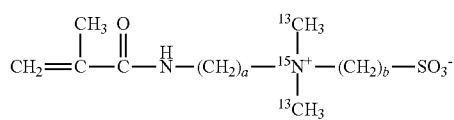
(j11)

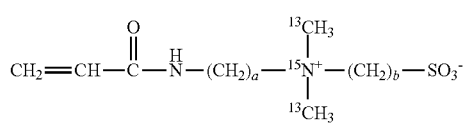
(j12)

wherein, in the formulas (j1) to (j12), each of a and b independently represents an integer of one or more and four or less, and a hydrogen atom of a methylene group is optionally replaced by another atom.

16. A method of nuclear magnetic resonance analysis, comprising detecting a polymer in a specimen, the method comprising:
preparing the polymer according to claim 1;
providing the polymer to the specimen; and
applying electromagnetic waves to the specimen provided with the polymer,
wherein magnetization transfer (coherence transfer) among nuclei in a $^1$H—$^{13}$C—$^{15}$N bond sequence, a $^1$H—$^{15}$N—$^{13}$C bond sequence or a $^1$H—$^{13}$C—$^{13}$C bond sequence of the polymer is utilized for detecting the polymer.

17. A method of magnetic resonance imaging, comprising detecting a position of a polymer in a specimen, the method comprising:
preparing the polymer according to claim 1;
providing the polymer to the specimen; and
applying electromagnetic waves to the specimen provided with the polymer,
wherein magnetization transfer (coherence transfer) among nuclei in a $^1$H—$^{13}$C—$^{15}$N bond sequence, a $^1$H—$^{15}$N—$^{13}$C bond sequence or a $^1$H—$^{13}$C—$^{13}$C bond sequence of the polymer is utilized for detecting the position of the polymer.

18. The method according to claim 16, wherein the magnetization transfer (coherence transfer) among nuclei in the $^1$H—$^{13}$C—$^{15}$N bond sequence is utilized.

19. The polymer according to claim 1, represented by formula (i1)

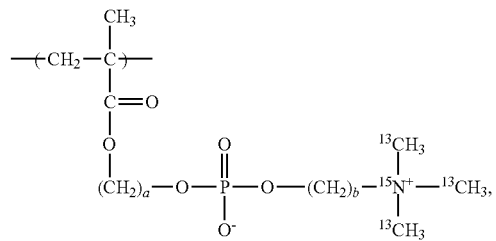
(i1)

wherein, in the formula (i1), a and b independently represents an integer of one to four, and a hydrogen atom of a methylene group is optionally replaced by another atom.

20. A compound comprising the polymer according to claim 1 and a scFv comprising an amino acid sequence represented by SEQ ID NO: 2.

21. The polymer according to claim 1,
wherein a terminal end group of one end of the main chain has a structure selected from the group consisting of formulas (b1) to (b9):

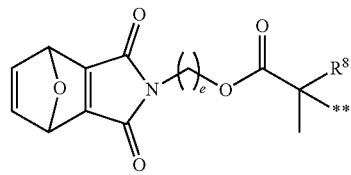
(b1)

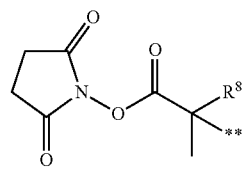
(b2)

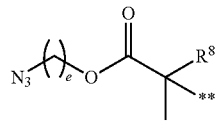
(b3)

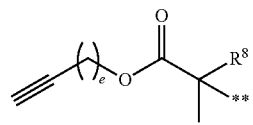
(b4)

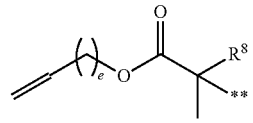
(b5)

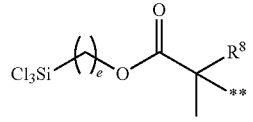
(b6)

-continued

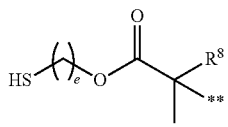
(b7)

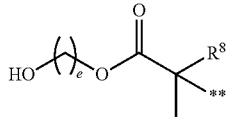
(b8)

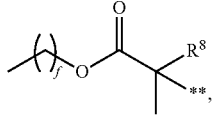
(b9)

wherein, in the formulas (b1) to (b9), e represents an integer of one to 11, f represents an integer of zero to 17, $R^8$ represents a hydrogen atom or a methyl group, and ** (two asterisks) represents a bond to the formula (x1).

22. The polymer according to claim 21, wherein a terminal end group of another end of the main chain is —Br.

23. The polymer according to claim 1, wherein a terminal end group of one end of the main chain is represented by formula (b1'):

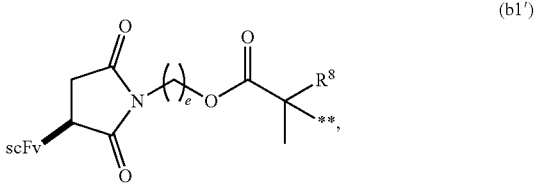
(b1')

wherein, in the formula (b1'), e represents an integer of one to 11, $R^8$ represents a hydrogen atom or a methyl group, ** (two asterisks) represents a bond to the formula (x1), and scFv is an amino acid sequence represented by SEQ ID NO: 2.

* * * * *

SEQUENCE LISTING

<160> NUMBER OF SEQ ID NOS: 2

<210> SEQ ID NO 1
<211> LENGTH: 739
<212> TYPE: DNA
<213> ORGANISM: Artificial Sequence
<220> FEATURE:
<223> OTHER INFORMATION: hu4D5-8scFv

<400> SEQUENCE: 1

```
ccatggatat ccagatgacc cagtccccga gctccctgtc cgcctctgtg ggcgataggg    60
tcaccatcac ctgccgtgcc agtcaggatg tgaatactgc tgtagcctgg tatcaacaga   120
aaccaggaaa agctccgaaa ctactgattt actcggcatc cttcctctac tctggagtcc   180
cttctcgctt ctctggatcc agatctggga cggatttcac tctgaccatc agcagtctgc   240
agccggaaga cttcgcaact tattactgtc agcaacatta ctactcctcc ccacgttcg    300
gacagggtac caaggtggag atcaaaggcg gtggtggcag cggtggcggt ggcagcggcg   360
gtggcggtag cgaggttcag ctggtggagt ctggcggtgg cctggtgcag cagggggct   420
cactccgttt gtcctgtgca gcttctggct tcaacattaa agacacctat atacactggg   480
tgcgtcaggc cccgggtaag ggcctggaat gggttgcaag gatttatcct acgaatggtt   540
atactagata tgccgatagc gtcaagggcc gtttcactat aagcgcagac acatccaaaa   600
acacagccta cctgcagatg aacagcctgc gtgctgagga cactgccgtc tattattgtt   660
ctagatgggg aggggacggc ttctatgcta tggactactg gggtcaagga accctggtca   720
ccgtctcctc ggcggccgc                                                739
```

<210> SEQ ID NO 2
<211> LENGTH: 256
<212> TYPE: PRT
<213> ORGANISM: Artificial Sequence
<220> FEATURE:
<223> OTHER INFORMATION: hu4D5-8scFv

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
```

-continued

|     |     |     | 165 |     |     |     | 170 |     |     |     | 175 |     |
| --- | --- | --- | --- | --- | --- | --- | --- | --- | --- | --- | --- | --- |
| Asn | Gly | Tyr | Thr | Arg | Tyr | Ala | Asp | Ser | Val | Lys | Gly | Arg | Phe | Thr | Ile |
|     |     |     |     | 180 |     |     |     |     | 185 |     |     |     |     | 190 |     |
| Ser | Ala | Asp | Thr | Ser | Lys | Asn | Thr | Ala | Tyr | Leu | Gln | Met | Asn | Ser | Leu |
|     |     | 195 |     |     |     |     | 200 |     |     |     |     | 205 |     |     |     |
| Arg | Ala | Glu | Asp | Thr | Ala | Val | Tyr | Tyr | Cys | Ser | Arg | Trp | Gly | Gly | Asp |
|     | 210 |     |     |     |     | 215 |     |     |     |     | 220 |     |     |     |     |
| Gly | Phe | Tyr | Ala | Met | Asp | Tyr | Trp | Gly | Gln | Gly | Thr | Leu | Val | Thr | Val |
| 225 |     |     |     |     | 230 |     |     |     |     | 235 |     |     |     |     | 240 |
| Ser | Ser | Ala | Ala | Ala | Leu | Glu | His | His | His | His | His | His | Gly | Gly | Cys |
|     |     |     |     | 245 |     |     |     | 250 |     |     |     |     | 255 |     |     |